United States Patent
Huynh et al.

(10) Patent No.: US 9,254,143 B2
(45) Date of Patent: Feb. 9, 2016

(54) GUIDEWIRE FOR CROSSING OCCLUSIONS OR STENOSES HAVING A SHAPEABLE DISTAL END

(75) Inventors: Christopher Huynh, San Jose, CA (US); Nestor Aganon, San Jose, CA (US); Michael Carley, San Jose, CA (US); Victor Chechelski, San Jose, CA (US); Rudolfo Sudaria, San Jose, CA (US)

(73) Assignee: REVASCULAR THERAPEUTICS, INC., Sunnyvale, CA (US)

( * ) Notice: Subject to any disclaimer, the term of this patent is extended or adjusted under 35 U.S.C. 154(b) by 1616 days.

(21) Appl. No.: 11/848,331

(22) Filed: Aug. 31, 2007

(65) Prior Publication Data

US 2008/0221601 A1    Sep. 11, 2008

Related U.S. Application Data

(63) Continuation-in-part of application No. 10/999,457, filed on Nov. 29, 2004, now abandoned, which is a continuation-in-part of application No. 09/644,201, filed on Aug. 22, 2000, now Pat. No. 6,824,550.

(60) Provisional application No. 60/195,154, filed on Apr. 6, 2000.

(51) Int. Cl.
| | | |
|---|---|---|
| *A61M 25/00* | (2006.01) | |
| *A61B 17/3207* | (2006.01) | |
| *A61B 17/00* | (2006.01) | |
| *A61B 17/22* | (2006.01) | |

(52) U.S. Cl.
CPC ... *A61B 17/320758* (2013.01); *A61B 2017/003* (2013.01); *A61B 2017/22044* (2013.01); *A61B 2017/320733* (2013.01)

(58) Field of Classification Search
CPC .............. A61B 17/320758; A61B 2017/22044
USPC .......................................... 600/585; 606/159
See application file for complete search history.

(56) References Cited

U.S. PATENT DOCUMENTS

| | | |
|---|---|---|
| 4,068,660 A | 1/1978 | Beck |
| 4,368,730 A | 1/1983 | Sharrock |
| 4,377,169 A | 3/1983 | Banks |
| 4,445,509 A | 5/1984 | Auth |
| 4,471,779 A | 9/1984 | Antoshkiw et al. |
| 4,490,421 A | 12/1984 | Levy |
| 4,516,972 A | 5/1985 | Samson |

(Continued)

OTHER PUBLICATIONS

International Search Report and Written Opinion of PCT Application No. PCT/US2008/073264, dated Nov. 12, 2008, 9 pages total.

(Continued)

*Primary Examiner* — Lee S Cohen
*Assistant Examiner* — Emily Lloyd
(74) *Attorney, Agent, or Firm* — Seager, Tufte & Wickhem LLP

(57) ABSTRACT

A hollow guidewire with a shapeable distal end, for removing tissue from a body lumen, such as a coronary artery. The hollow guidewire comprises an elongate, tubular guidewire body that has an axial lumen. A tissue removal assembly, such as a rotating drive shaft, is positioned at or near a distal end of the tubular guidewire body and extends through the axial lumen. Actuation of the tissue removal assembly removes occlusive material in the body lumen.

29 Claims, 16 Drawing Sheets

(56) References Cited

U.S. PATENT DOCUMENTS

| | | |
|---|---|---|
| 4,534,363 A | 8/1985 | Gold |
| 4,538,622 A | 9/1985 | Samson et al. |
| 4,545,390 A | 10/1985 | Leary |
| 4,548,206 A | 10/1985 | Osborne |
| 4,554,929 A | 11/1985 | Samson et al. |
| 4,573,470 A | 3/1986 | Samson et al. |
| 4,586,923 A | 5/1986 | Gould et al. |
| 4,601,705 A | 7/1986 | McCoy |
| 4,613,385 A | 9/1986 | Thomas et al. |
| 4,616,653 A | 10/1986 | Samson et al. |
| 4,619,263 A | 10/1986 | Frisbie et al. |
| 4,641,654 A | 2/1987 | Samson et al. |
| 4,646,719 A | 3/1987 | Neuman et al. |
| 4,646,742 A | 3/1987 | Packard et al. |
| 4,676,249 A | 6/1987 | Arenas et al. |
| 4,708,717 A | 11/1987 | Deane et al. |
| 4,708,718 A | 11/1987 | Daniels |
| 4,715,378 A | 12/1987 | Pope, Jr. et al. |
| 4,717,387 A | 1/1988 | Inoue et al. |
| 4,719,924 A | 1/1988 | Crittenden et al. |
| 4,721,117 A | 1/1988 | Mar et al. |
| 4,723,936 A | 2/1988 | Buchbinder et al. |
| 4,739,768 A | 4/1988 | Engelson |
| 4,763,647 A | 8/1988 | Gambale |
| 4,767,400 A | 8/1988 | Miller et al. |
| 4,779,628 A | 10/1988 | Machek |
| 4,781,486 A | 11/1988 | Mochizuki |
| 4,798,598 A | 1/1989 | Bonello et al. |
| 4,832,047 A | 5/1989 | Sepetka et al. |
| 4,846,186 A | 7/1989 | Box et al. |
| 4,899,787 A | 2/1990 | Ouchi et al. |
| 4,906,241 A | 3/1990 | Noddin et al. |
| 4,923,462 A | 5/1990 | Stevens |
| 4,925,445 A | 5/1990 | Sakamoto et al. |
| 4,926,858 A | 5/1990 | Gifford, III et al. |
| 4,940,062 A | 7/1990 | Hampton et al. |
| 4,946,466 A | 8/1990 | Pinchuk et al. |
| 4,953,553 A * | 9/1990 | Tremulis .................. 600/585 |
| 4,979,939 A | 12/1990 | Shiber |
| 4,990,134 A | 2/1991 | Auth |
| 5,021,044 A | 6/1991 | Sharkawy |
| 5,030,204 A | 7/1991 | Badger et al. |
| 5,041,082 A | 8/1991 | Shiber |
| 5,041,085 A | 8/1991 | Osborne et al. |
| 5,059,851 A | 10/1991 | Corl et al. |
| 5,060,660 A | 10/1991 | Gambale et al. |
| 5,067,489 A | 11/1991 | Lind |
| 5,107,852 A | 4/1992 | Davidson et al. |
| 5,115,814 A | 5/1992 | Griffith et al. |
| 5,116,350 A | 5/1992 | Stevens |
| 5,144,959 A | 9/1992 | Gambale et al. |
| 5,165,421 A | 11/1992 | Fleischhacker et al. |
| 5,176,661 A | 1/1993 | Evard et al. |
| 5,178,158 A | 1/1993 | de Toledo |
| 5,184,627 A | 2/1993 | de Toledo |
| 5,195,971 A | 3/1993 | Sirhan |
| 5,209,727 A | 5/1993 | Radisch, Jr. et al. |
| 5,211,636 A | 5/1993 | Mische |
| 5,217,482 A | 6/1993 | Keith |
| 5,250,034 A | 10/1993 | Appling et al. |
| 5,267,979 A | 12/1993 | Appling et al. |
| 5,306,252 A | 4/1994 | Yutori et al. |
| 5,314,438 A | 5/1994 | Shturman |
| RE34,695 E | 8/1994 | Mar et al. |
| 5,344,395 A * | 9/1994 | Whalen et al. ............. 606/159 |
| 5,345,945 A | 9/1994 | Hodgson et al. |
| 5,346,473 A | 9/1994 | Bowman |
| 5,368,035 A | 11/1994 | Hamm et al. |
| 5,377,690 A | 1/1995 | Berthiaume |
| 5,378,234 A | 1/1995 | Hammerslag et al. |
| 5,391,147 A | 2/1995 | Imran et al. |
| 5,462,523 A | 10/1995 | Samson et al. |
| 5,484,407 A | 1/1996 | Osypka |
| 5,527,298 A | 6/1996 | Vance et al. |
| 5,527,326 A | 6/1996 | Hermann et al. |
| 5,531,677 A | 7/1996 | Lundquist et al. |
| 5,569,197 A | 10/1996 | Helmus et al. |
| 5,571,085 A | 11/1996 | Accisano, III |
| 5,591,142 A | 1/1997 | Van Erp |
| 5,606,981 A | 3/1997 | Tartacower et al. |
| 5,611,777 A | 3/1997 | Bowden et al. |
| 5,632,755 A | 5/1997 | Nordgren et al. |
| 5,651,785 A | 7/1997 | Abela et al. |
| 5,662,671 A | 9/1997 | Barbut et al. |
| 5,702,373 A | 12/1997 | Samson |
| 5,772,609 A | 6/1998 | Nguyen et al. |
| 5,776,114 A | 7/1998 | Frantzen et al. |
| 5,820,591 A | 10/1998 | Thompson et al. |
| 5,843,103 A | 12/1998 | Wulfman |
| 5,848,986 A | 12/1998 | Lundquist et al. |
| 5,860,938 A | 1/1999 | LaFontaine et al. |
| 5,865,800 A | 2/1999 | Mirarchi et al. |
| 5,868,685 A | 2/1999 | Powell et al. |
| 5,897,567 A | 4/1999 | Ressemann et al. |
| 5,908,395 A | 6/1999 | Stalker et al. |
| 6,001,112 A | 12/1999 | Taylor |
| 6,022,336 A | 2/2000 | Zadno-Azizi et al. |
| 6,050,972 A | 4/2000 | Zadno-Azizi et al. |
| 6,059,767 A | 5/2000 | Noriega |
| 6,066,149 A | 5/2000 | Samson et al. |
| 6,068,623 A | 5/2000 | Zadno-Azizi et al. |
| 6,093,157 A | 7/2000 | Chandrasekaran |
| 6,143,009 A | 11/2000 | Shiber |
| 6,152,909 A | 11/2000 | Bagaoisan et al. |
| 6,156,046 A | 12/2000 | Passafaro et al. |
| 6,179,851 B1 | 1/2001 | Barbut et al. |
| 6,183,432 B1 | 2/2001 | Milo |
| 6,193,735 B1 * | 2/2001 | Stevens .................. 606/159 |
| 6,217,567 B1 | 4/2001 | Zadno-Azizi et al. |
| 6,258,052 B1 | 7/2001 | Milo |
| 6,299,622 B1 | 10/2001 | Snow et al. |
| 6,312,438 B1 | 11/2001 | Adams |
| 6,355,014 B1 | 3/2002 | Zadno-Azizi et al. |
| 6,375,628 B1 | 4/2002 | Zadno-Azizi et al. |
| 6,482,221 B1 | 11/2002 | Hebert et al. |
| 6,500,130 B2 | 12/2002 | Kinsella et al. |
| 6,533,749 B1 | 3/2003 | Mitusina et al. |
| 6,585,717 B1 | 7/2003 | Wittenberger et al. |
| 6,602,264 B1 | 8/2003 | McGuckin, Jr. |
| 6,652,508 B2 | 11/2003 | Griffin et al. |
| 6,743,208 B1 | 6/2004 | Coyle |
| 6,746,422 B1 | 6/2004 | Noriega et al. |
| 6,824,550 B1 | 11/2004 | Noriega et al. |
| 2004/0111044 A1 * | 6/2004 | Davis et al. .................. 600/585 |
| 2005/0020974 A1 | 1/2005 | Noriega et al. |
| 2005/0113853 A1 | 5/2005 | Noriega et al. |
| 2006/0074442 A1 | 4/2006 | Noriega et al. |
| 2006/0241519 A1 | 10/2006 | Hojeibane et al. |

OTHER PUBLICATIONS

International Search Report and Written Opinion of PCT Application No. PCT/US05/42763, dated Mar. 6, 2008, 13 pages total.

* cited by examiner

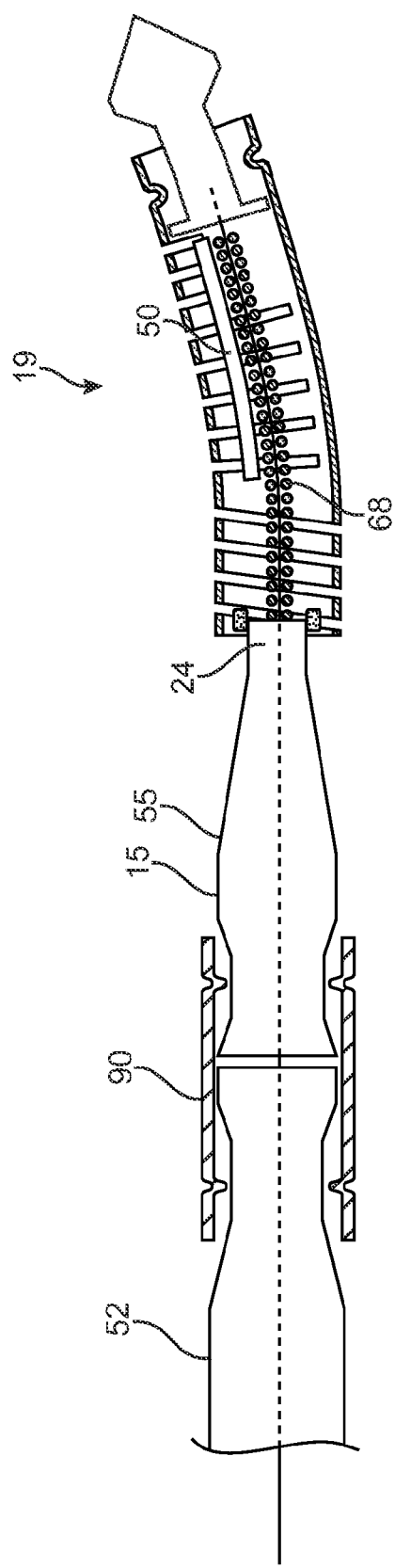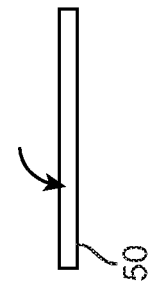
FIG. 4
FIG. 4A
FIG. 4B

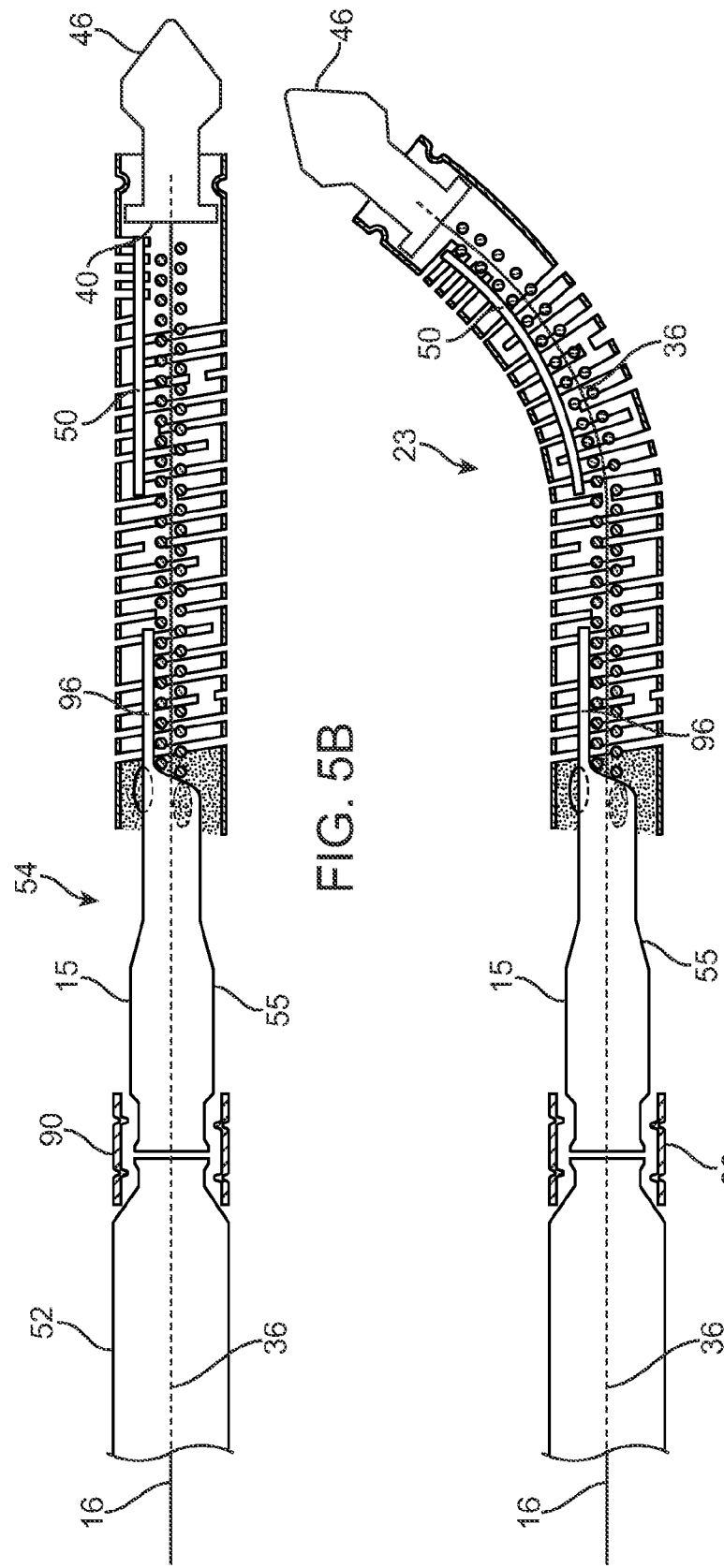

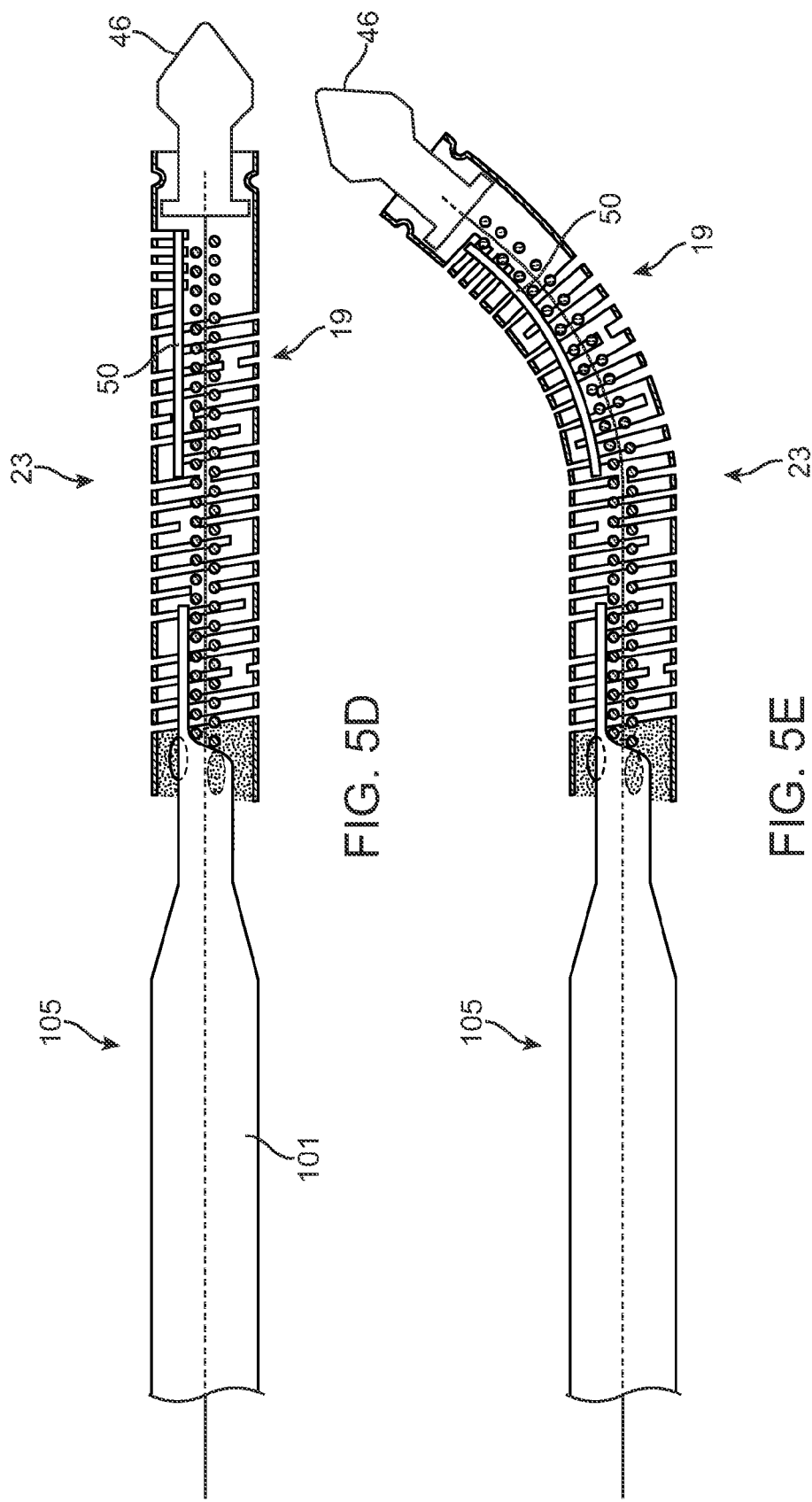

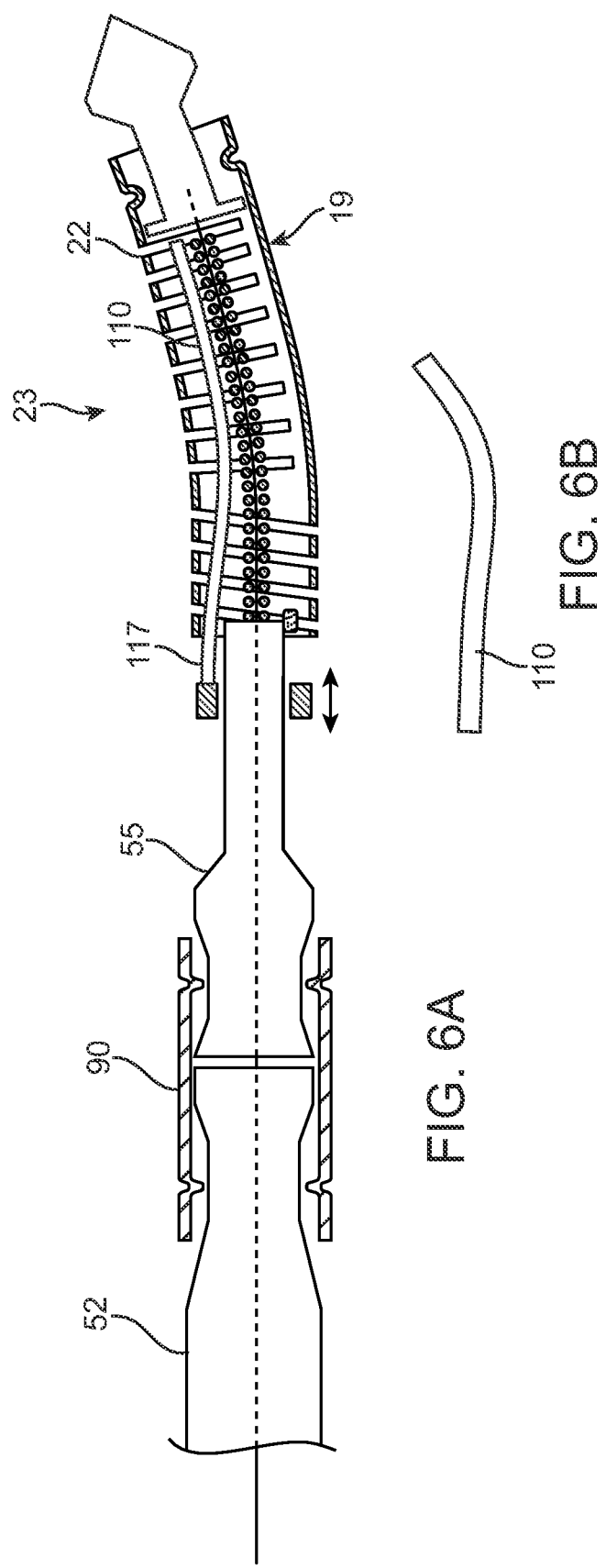

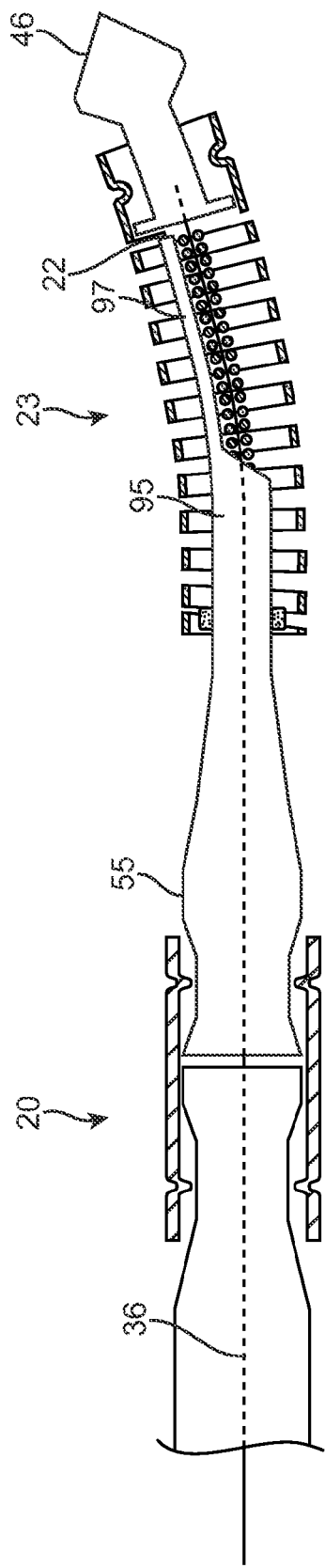
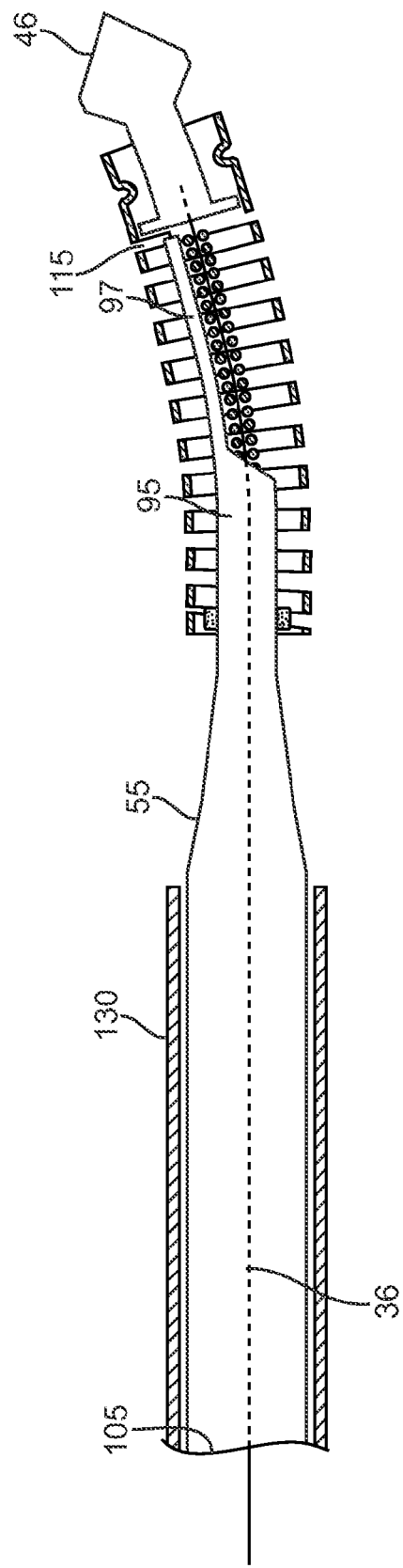
FIG. 9
FIG. 10

GUIDEWIRE FOR CROSSING OCCLUSIONS OR STENOSES HAVING A SHAPEABLE DISTAL END

CROSS-REFERENCES TO RELATED APPLICATIONS

The present application is a continuation-in-part of U.S. patent application Ser. No. 10/999,457 filed Nov. 29, 2004 now abandoned, which is continuation-in-part of U.S. patent application Ser. No. 09/644,201 filed Aug. 22, 2000 now U.S. Pat. No. 6,824,550, which claimed the benefit under 37 C.F.R. §1.78 to U.S. Provisional Patent Application No. 60/195,154 filed Apr. 6, 2000 the complete disclosures of which are incorporated herein by reference.

The present application is also related to U.S. patent application Ser. No. 09/030,657, filed Feb. 25, 1998, entitled "Steerable Unitary Infusion Catheter/Guide Wire Incorporating Detachable Infusion Port Assembly," and now U.S. Pat. No. 6,059,767, and U.S. patent application Ser. No. 09/935,534, filed Aug. 22, 2001, entitled "Steerable Support System with External Ribs/Slots that Taper," and now U.S. Pat. No. 6,746,422, the complete disclosures of which are incorporated herein by reference, in their entirety. The present application is also related to U.S. patent application Ser. No. 11/236,703, filed Sep. 26, 2005, entitled "Guidewire for Crossing Occlusions or Stenoses," which was a continuation-in-part of U.S. patent application Ser. No. 10/999,457, filed Nov. 29, 2004, entitled "Guidewire For Crossing Occlusions or Stenoses," which was a continuation-in-part of U.S. patent application Ser. No. 09/644,201, filed Aug. 22, 2000, entitled "Guidewire for Crossing Occlusions or Stenoses," and now U.S. Pat. No. 6,824,550, which claimed the benefit under 37 C.F.R. § 1.78 to U.S. Provisional Patent Application No. 60/195,154, filed Apr. 6, 2000, entitled "Guidewire for Crossing Occlusions or Stenosis," U.S. patent application Ser. No. 11/388,251, filed Mar. 22, 2006, entitled "Guidewire Controller System," and U.S. patent application Ser. No. 11/567,884, filed on Dec. 12, 2006, entitled "Apparatus for Crossing Occlusions or Stenoses"; the complete disclosures of all aforementioned are incorporated herein by reference, in their entirety.

BACKGROUND OF THE INVENTION

The present invention is generally related to medical devices, kits, and methods. More specifically, the present invention provides a guidewire system for crossing stenosis, partial occlusions, or total occlusions in a patient's body.

Cardiovascular disease frequently arises from the accumulation of atheromatous material on the inner walls of vascular lumens, particularly arterial lumens of the coronary and other vasculature, resulting in a condition known as atherosclerosis. Atheromatous and other vascular deposits restrict blood flow and can cause ischemia which, in acute cases, can result in myocardial infarction or a heart attack. Atheromatous deposits can have widely varying properties, with some deposits being relatively soft and others being fibrous and/or calcified. In the latter case, the deposits are frequently referred to as plaque. Atherosclerosis occurs naturally as a result of aging, but may also be aggravated by factors such as diet, hypertension, heredity, vascular injury, and the like.

Atherosclerosis can be treated in a variety of ways, including drugs, bypass surgery, and a variety of catheter-based approaches which rely on intravascular widening or removal of the atheromatous or other material occluding the blood vessel. Particular catheter-based interventions include angioplasty, atherectomy, laser ablation, stenting, and the like. For the most part, the catheters used for these interventions must be introduced over a guidewire, and the guidewire must be placed across the lesion prior to catheter placement. Initial guidewire placement, however, can be difficult or impossible in tortuous regions of the vasculature. Moreover, it can be equally difficult if the lesion is total or near total, i.e. the lesion occludes the blood vessel lumen to such an extent that the guidewire cannot be advanced across the lesion.

To overcome this difficulty, forward-cutting atherectomy catheters have been proposed. Such catheters usually can have a forwardly disposed blade (U.S. Pat. No. 4,926,858) or rotating burr (U.S. Pat. No. 4,445,509). While effective in some cases, these catheter systems, even when being advanced through the body lumen with a separate guidewire, have great difficulty in traversing through the small and tortuous body lumens of the patients and reaching the target site.

For these reasons, it is desired to provide devices, kits, and methods which can access small, tortuous regions of the vasculature and which can remove atheromatous, thrombotic, and other occluding materials from within blood vessels. In particular, it is desired to provide atherectomy systems which can pass through partial occlusions, total occlusions, stenosis, and be able to macerate blood clots or thrombotic material. It is further desirable to have devices which can easily be configured by the user to have the desired shapeability and/or flexibility. At least some of these needs will be met by the devices and methods of the present invention described hereinafter and in the claims.

BRIEF SUMMARY OF THE INVENTION

The systems, devices and methods according to the present invention will generally be adapted for the intraluminal treatment of a target site within a body lumen of a patient, usually in a coronary artery or peripheral blood vessel which is occluded or stenosed with atherosclerotic, stenotic, thrombotic, or other occlusive material. The systems, devices and methods, however, are also suitable for treating stenoses of the body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed at passing through atheromatous or thrombotic occlusive material in a coronary and peripheral arteries, it will be appreciated that the systems and methods of the present invention can be used to remove and/or pass through a variety of occlusive, stenotic, or hyperplastic material in a variety of body lumens. It should also be appreciated, that many of the features of the different embodiments as described, may be used in the described embodiment or together with others. More particularly, the present invention can be used for passing through stenosis or occlusions in a neuro, cardio, and peripheral body lumens.

The present invention provides for a manually shapeable hollow guidewire for crossing an occlusion or stenosis within a body lumen. The shaped end will have the ability to retain its shape even as the guidewire is advanced through a tortuous body lumen and as an internal core wire is rotated within a central passage of the body. In addition, the shaped end as well as the proximal portions of the guidewire will provide a stable platform as the core wire is rotated, generally avoiding unwanted oscillations and rotation of the distal end of the body of the guidewire. While particularly intended for advancement through calcified and difficult lesions, the shapeable guidewires of the present invention can also be advanced and otherwise used while the core wire is not being rotated.

Generally, the present invention includes an elongate member, such as a hollow body guidewire, i.e., having a central passage extending at least partially from the proximal end to the distal end, and having a shapeable (or malleable) distal region, that is advanced through a body lumen and positioned adjacent the occlusion or stenosis. The hollow devices of the present invention, unless otherwise stated, may generally have similar dimensions as those of conventional guidewires. Devices of the present invention, such as hollow guidewire devices, may be used alone or in combination with other elongate members such as conventional guidewires and access systems.

In an embodiment, the guidewire, comprises a guidewire body having a proximal end, a distal end, and a central passage therethrough. A distal region of the body is malleable (shapeable) so that it may be manually configured to a desired shape. A mechanically driven core element disposed in the central passage and passes out through the distal end of the guidewire body. The core element may be rotated, oscillated, and/or translated within the central passage while the distal region of the body retains its desired shape. In an embodiment, malleable distal region comprises a tube formed from a malleable metal. The tube may be slotted at least along a portion of its length.

In an embodiment, the slots are formed along a helical spine In an embodiment, the slots are formed along an axial spine. The tube may be cut into a helical ribbon along at least a portion of its length. In an embodiment, the slots along the helical spine have interruptions.

In some embodiments, a spring element is disposed along at least a portion of the malleable distal region. The spring is aligned to help hold a desired shape at the shapeable distal region. The spring may be a linear spring axially aligned along one side of at least the malleable distal region with the spring having an arcuate memory to help an arc manually formed in the malleable region. In some embodiments, the spring element is formed from a shape memory material.

In some embodiments, the malleable distal region comprises a heat-sensitive component that can be softened by heating. The heat-sensitive component may include, but is not limited to a polymer jacket disposed along at least a portion of the malleable distal region.

The malleable distal region and the core element may be at least partially separated by a liner, as for example, a coil. The core element includes a drive shaft formed from, at least in part, from nickel titanium, and a distal tip, which normally extends distal of the distal tip of the guidewire body.

The distal end of the guidewire will preferably be sufficiently pushable so that it may be advanced through an occlusion or stenosed region in the blood vessel or other lumen being treated. The distal end, however, must not be so stiff that it is difficult to advance the guidewire through tortuous luminal regions, such as in the coronary vasculature. It is particularly preferred that a distal most 10 mm of the guidewire have a column strength (pushability) in the range from 3 g to 50 g, usually from 6 g to 35 g. The column strength may be measured by clamping the guidewire at a location 10 mm proximal of the distal tip. A force gage is then pushed against the distal tip and the force, in grams, is monitored until the guidewire first begins to buckle anywhere alone the exposed 10 mm. The force at the initial point of buckling will be considered the column strength of the guidewire.

The guidewire body is formed from either or both a first and a second solid walled tube. The first solid walled tube may extend proximally from at least a longitudinal portion of the malleable region to the proximal end of the guidewire. Additionally, or alternatively, the, first solid walled tube may extend proximally from at least a longitudinal portion of the malleable region, and a distal end of the second solid walled tube which extends to the proximal end of the guidewire.

In an exemplary embodiment, the first solid walled tube and the second solid walled tubes may be formed from suitable materials such as, respectively, nickel titanium and stainless steel. A housing is disposed at the proximal end of the guidewire tube and contains a motor for moving the core element. The motor may be attached to a controller system. In an embodiment the proximal end of the guidewire body is configured for attachment to a distal end of an extension body.

In methods for practicing the invention, embodying features of the present invention, method for crossing a luminal occlusion, said method includes providing a shapeable hollow guidewire, as described above and manually shaping a distal end of the guidewire. The guidewire is advanced through an occlusion while a core element carried by the guidewire is mechanically driven to engage and penetrate the occlusion while the core holds the shape defined by the manually shaped distal end of the guidewire.

In another embodiment the body lumen, embodying features of the present invention includes a guidewire body having a proximal end, a distal end, and a central passage therethrough, and a distal region which is shapeable (e.g., malleable) by the user to a desired shape. The distal shapeable region may be manually or otherwise shaped, by suitable means. A mechanically driven core element is disposed in the central passage of the body and exists out of the distal end of the guidewire body. The core element may be rotated, oscillated, axially movable, or any combination thereof, while the distal region of the body retains its desired shape. In an embodiment, the malleable ("shapeable") distal region includes a tube formed from a malleable or shapeable metal. In an embodiment, the tube is slotted along at least a portion of its length. The slots may be formed along a helical spine. In an embodiment the slots are formed along an axial spine.

In an embodiment, the tube is cut into helical ribbon (helix with interruptions) along at least a portion of its length. In various embodiments, the hollow guidewire includes a spring element disposed along the malleable (shapeable) distal region. The spring element is aligned to help the shapeable distal region in holding the desired shape. In some embodiments, the spring is a linear spring axially aligned along one side of the malleable distal region, with the spring having an arcuate memory which helps hold an arc manually formed in the malleable region.

In an embodiment, the malleable distal region includes a heat sensitive component that can be softened by heating. In an embodiment, the heat sensitive component may include a polymer jacket formed over the malleable distal region.

The present invention is further directed to methods crossing luminal occlusions. In an embodiment, the method includes providing a shapeable hollow guidewire, manually shaping a distal section of the guidewire, advancing the guidewire through an occlusion. A core element carried by the guidewire is mechanically driven to engage and penetrate the occlusion while the core element maintains the shape of the shapeable distal region of the guidewire.

In an embodiment, the distal tip of the core element may be configured for further advancement and/or retraction from the distal end of the hollow guidewire. Once the guidewire has reached the lesion, the guidewire with the exposed drive shaft may be advanced into the lesion. Alternatively, the guidewire may be disposed in a relatively fixed position, and the drive shaft may be advanced to create an opening forward of the hollow guidewire forming a path in the occlusion or stenosis. In an embodiment, the core element is configured for rotational oscillation.

The shapeable distal region of the guidewire body, as shaped by the user, according to the present invention, may range from about 0° degrees ("°") to about 90°, from about 0° to about 60°, from about 0° to about 45°, from about 5° to about 45°. The length of the shapeable region may range from about 0.1 centimeter ("cm") to 4.0 cm, from about 0.2 cm to about 2.0 cm, from about 0.3 cm, to about 1.0 cm. The angle after the distal shapeable region of the hollow guidewire body has been shaped, may be arrived at in a smooth transition or in an abrupt transition, or any type and degree of transition in-between. One or more shapes may be placed into the distal section of the guidewire body. In an embodiment, the distal 0.5 cm may be shaped to 30°, and a 15° angle may be placed over 0.5 cm proximal to the 30° angle. To facilitate passing through the occlusion or stenosis, the distal section of the hollow guidewire can be steerable. Optionally, the target site can be infused and/or aspirated before, during, and after creation of the path through the occlusion.

In an embodiment, the shapeability of the distal region is, at least in part, achieved by way of an elongate body such as a metal wire or ribbon (or spring) longitudinally disposed within the distal end of the body of the hollow guidewire inner lumen. The spring is optionally fixedly attached to an inner surface of the body. The elongate body/spring is formed from a shape memory material having an arcuate memory. In an embodiment, the metal wire or ribbon/spring is attached to the inner lumen along at least a distal attachment point at the hollow guidewire distal end. The elongate body/spring conforms to the inner diameter of the distal portion of the hollow guidewire when it is attached thereto by suitable means, such as soldering. The metal wire or ribbon/spring (with flat or curved profile) may be formed from suitable material such as stainless steel, nitinol, or cobalt-chromium; and has a longitudinal dimension ranging from about 0.1 centimeters ("cm") to about 4 cm, from about 0.2 cm to about 1 cm. In an embodiment, the metal wire or ribbon has a longitudinal dimension of about 0.3 cm.

In an embodiment, the shapeable (malleable) distal region is, at least in part, achieved by way of a shaped distal portion of the guidewire body. For example, the shaped distal portion may be made from a nickel-titanium alloy and heat set to a desired deflection angle. In such an embodiment, the distal portion may, optionally, also include the elongate body such as the metal wire or ribbon/spring as further means to provide the desirable deflection.

The hollow guidewire of the present invention has a shapeable (malleable) distal region, flexibility, pushability, and torqueability to be advanced through the tortuous blood vessel without the use of a separate guidewire or other guiding element. Additionally, the hollow guidewire may be sized to fit within an axial lumen of a conventional support or access catheter system. The distal end deflection is designed such that when the guidewire is housed within and introduced through another elongate body, such as a balloon catheter, the angle of the distal end of the guidewire is straight (e.g., straightened) to accommodate the inner diameter of the catheter. Once the guidewire exits the catheter (e.g., balloon catheter), the distal end returns to its shaped angle.

The catheter system can be delivered either concurrently with the advancement of the hollow guidewire or after the hollow guidewire or conventional guidewire has reached the target site. The core element as disposed within the axial lumen of the hollow guidewire and extending distally from the guidewire distal end may be rotated, preferably oscillating between a set number of rotations into the occlusion. In an embodiment, the distal tip of the core element may be configured for further advancement and/or retraction from the distal end of the hollow guidewire, such that the position of the hollow guidewire and catheter system can be maintained and stabilized while the core element is rotated and translated out of the axial lumen of the hollow guidewire.

The distal tip of the core element may be coiled, blunted, flattened, enlarged, twisted, basket shaped, football shaped, bullet shaped, coned shaped, or the like. In some embodiments, to increase the rate of removal of the occlusive material, the distal tip is sharpened or impregnated with an abrasive material such as diamond chips, diamond powder, glass, or the like. The core element distal tip may be formed of any suitable material such as stainless steel, nitinol, cobalt-chromium, polymeric material, or radiopaque material such as platinum-iridium. In an embodiment, the core element distal tip may be formed from a composite material such as a stainless steel tip having a cavity filled with a radiopaque material. Alternatively, or in addition thereto, the plaque removal assembly may comprise a laser, an RF electrode, a heating element (e.g., resistive element), an ultrasound transducer, or the like. A lead of the plaque removal assembly may extend proximally through the axial lumen of the hollow guidewire body. In an embodiment, the drive shaft is distally tapered, as for example along the shaped distal end of the guidewire body.

The hollow guidewire body includes proximal and distal portions. In an embodiment, the elongate hollow guidewire body may be formed from a unitary tube having different portions. Alternatively, the guidewire body may be formed from several members joined longitudinally to one another forming the various portions. In an embodiment, the distal portion of the guidewire body comprises one or more patterns such as, but not limited to, interrupted helical pattern and ribbed pattern. Either of the patterned portions may extend proximally from the distal end of the hollow guidewire body with the other pattern extending proximally from a proximal end of the other. Alternatively, the guidewire distal portion may comprise a single type of pattern. In an embodiment, the interrupted helical patterned portion comprises laser edged helical windings formed at 180° interrupted by 30° segments. In an embodiment, the one or more patterned portions, together, have a longitudinal dimension ranging from about 0.3 to about 10 cm, from about 1 to about 5 cm, normally about 4 cm. In an embodiment, interrupted helical pattern is laser cut into a stainless steel tube. In an embodiment, all or at least a portion of the shapeable distal portion may be plated with suitable radiopaque material, such as gold.

In an embodiment, the guidewire body is formed from more than one tubular member. The distal tubular member is formed from a stainless steel tube with a laser cut helix with interruptions in at least a portion of the tube The distal tubular member includes a shapeable distal region and optionally a non-shapeable region (or less shapeable as compared to the shapeable distal region). An intermediate tubular member is located proximal to the distal tubular member. The intermediate tubular member and distal tubular members may be joined. The intermediate tubular member may be made from nitinol and distally tapered for increased distal flexibility. The intermediate tubular member may further be tapered within the distal tubular member to provide a smooth transition. The intermediate tubular member may extend all the way proximally into the housing or may be coupled to a proximal tubular member formed from suitable material such as stainless steel. The intermediate tubular member and the proximal tubular member may be coupled together by suitable means such as a cuff, with the proximal tubular member extending into the housing.

In an embodiment, the intermediate tubular member may be at least partially covered with a coil or polymer (e.g, PEBAX). The longitudinal dimension extending between the distal tip of the core element to the proximal end of the exposed intermediate tubular member includes the flexible distal section.

In an embodiment, the flexible distal section has a longitudinal dimension ranging from about 1 to about 200 cm, from about 20 to about 200 cm, normally about 30 to 165 cm. While the material described above with respect to one or more embodiments, it should be appreciated than any tubular members may be independently formed from suitable material such as stainless steel, nitinol, polymeric material, or radiopaque material such as platinum-iridium or cobalt-chromium.

In an embodiment, a spring (e.g., a first tube forming at least in part a part of the intermediate portion) extends within at least a portion of the guidewire axial lumen. In an embodiment, the elongate tube may have flat or arcuate transverse profile, and may be coupled to the guidewire body distal end. The elongate tube may be distally tapered at the distal end. The elongate tube tapered distal end may be in the form of a ribbon/spring. The tapered distal end may have a flat or arcuate (e.g., crescent shape) transverse profile. In an embodiment, the elongate tube is skived at the distal end to provide the tapered distal end. The elongate tube generally has a longitudinal dimension ranging from about 1 to about 200 cm, from about 20 to about 190 cm, normally about 170 cm.

In an embodiment, the elongate tube (e.g., first tube) is tapered along the length of the flexible distal section of the hollow guidewire. In an embodiment, the tapered elongate tube terminates proximally at the proximal end of the flexible distal section. In an embodiment, the proximal end of the tapered elongate tube terminates within a solid wall tube which extends to the hollow guidewire proximal end. A distal end of the solid wall tube may form a distal flange extending over the proximal end of the elongate tube forming a joint (e.g., a lap joint) therewith.

The one or more portions of the elongate tube may be independently formed from any suitable material such as stainless steel, nickel-titanium alloy (such as nitinol), radiopaque material (such as platinum-iridium material), cobalt chromium, polymer (such as PEEK), or any combination thereof.

In an embodiment, a liner (e.g., a coil) coil is disposed about the distal portion of the drive shaft radially separating it from the inner surface of the hollow guidewire body. In an embodiment, the coil extends along the tapered distal portion of the elongate tube. The coil may be formed from any suitable material such as stainless steel, nickel-titanium alloy (such as nitinol), radiopaque material (such as platinum-iridium material), cobalt chromium, or any combination thereof. The coil may have a longitudinal dimension ranging from about 1 to about 60 millimeter ("mm"), from about 10 to about 50 mm, normally about 40 mm. In an embodiment, the coil (liner) extends distally about the drive shaft to the proximal end of the core element distal tip.

The drive shaft may be of a single wire type, a counter-wound guidewire construction, or be formed from a composite structure comprising a fine wire around which a coil is wrapped. In an embodiment, at least a portion of the drive shaft may be coated with lubricious material to enhance its movement within the inner lumen of the body.

The dimensions of the hollow guidewires of the present invention may vary depending on the target lumen, with the body and the specific needs of the procedure. In an embodiment, the radial dimension (e.g., outer diameter) of the guidewire body ranges from about 0.040 to about 0.008 inches ("in."), from about 0.035 to about 0.008 in., from about 0.024 to about 0.008 in., normally from about 0.018 to about 0.009 in. A wall thickness of the hollow guidewires of the present invention typically range from about 0.001 to about 0.004 in., but as with the other dimensions may vary depending on the desired characteristics of the hollow guidewire.

Systems and kits of the present invention may include a support system or access system, such as a catheter, having a body adapted for intraluminal introduction to the target blood vessel. The dimensions and other physical characteristics of the access system body will vary significantly depending on the body lumen which is to be accessed. The body of the support or access system is very flexible and is suitable for introduction over a conventional guidewire, or the hollow guidewire (e.g., having a removable handle) of the present invention. The support or access system body can either be for "over-the-wire" introduction or for "rapid exchange," where the guidewire lumen extends only through a distal portion of the access system body. Optionally, the support or access system can have at least one axial channel extending through the lumen to facilitate infusion to and/or aspiration of material from the target site. Support or access system bodies will typically be formed from an organic polymer, such as polyvinylchloride, polyurethanes, polyesters, polytetrafluoroethylenes (PTFE), silicone rubbers, natural rubbers, or the like. Suitable bodies may be formed by extrusion, with one or more lumens that extend axially through the body. For example, the support or access system can be a support catheter, interventional catheter, balloon dilation catheter, atherectomy catheter, rotational catheter, extractional catheter, laser ablation catheter, guiding catheter, stenting catheter, ultrasound catheter, and the like. The support system, which is described in more detail in commonly owned U.S. patent application Ser. No. 10/864,075, filed Jun. 8, 2004, the disclosure of which is incorporated herein by reference in its entirety, may be used for over-the-wire introduction or for rapid exchange.

The position of the hollow guidewire and/or support system may be maintained and stabilized during the advancing of the distal tip of the drive shaft. At the end of the plaque removal, the method may further comprise exchanging the hollow guidewire with the conventional guidewire. Additionally, other features of the devices of the present invention and methods using the same, are further described in commonly owned U.S. patent application Ser. No. 11/236,703, filed Sep. 26, 2005, and assigned to the assignee of the present invention, the disclosure of which is incorporated herein by reference in its entirety. In an embodiment, when the handle assembly is removably attached to the hollow guidewire, the handle assembly may be detached from the hollow guidewire (e.g., with the use of a guidewire extension) and the support catheter is removed and exchanged with another support catheter.

In an embodiment, the proximal end of the elongate member is housed within a handle assembly with proximal and distal ends, and a housing disposed therebetween. At the distal end, the handle assembly includes a strain relief having a lumen extending therethrough. A torquer with a lumen is disposed between the strain relief and the housing. The proximal end of the guidewire with the drive shaft proximal end disposed through the guidewire lumen, extends through the strain relief and the torquer. The proximal end of the guidewire terminates and is secured in place within a connector assembly which is located within the housing. The connector assembly limits the motion of the elongate member while allowing the drive shaft to either or both rotationally oscillate and translate within the elongate member. The proximal end of the drive shaft extends proximally from the connector assembly and is secured by a shaft coupling within the housing. In an embodiment, a motor disposed within the housing provides rotational oscillation to the drive shaft during operation. A connector cable connects the motor for moving (i.e., oscillate, rotate, translate, reciprocate, vibrate, or the like) the drive shaft and its distal tip, to a control system and power supply. It should be appreciated that the various components may be located within or outside of the housing. By way of example, the control system may be placed within the housing. Similarly, the power supply may be battery operated and similarly and entirely locatable within the housing.

The handle assembly may be removably or fixedly attached to the proximal ends of the hollow guidewire and the drive shaft. Optionally, some embodiments of the connector assembly include an aspiration or infusion port (not shown) for facilitating fluid exchange (e.g., delivery or removal) at the target site through the axial lumen.

Torque transmission of the guidewire body and activation of the core element may be carried out sequentially or simultaneously as a physician steers through a tortuous blood vessel. This can advantageously be accomplished while maintaining the handle in a stationary configuration that is ergonomically easy to grasp and control. The handle may further comprise a drive motor to move (e.g., oscillate, reciprocate, translate, rotate, vibrate, or the like) the core element, actuators for steering the guidewire body, a control system including circuitry which provides feedback control as discussed in more detail below, and/or a power supply. The handle may alternatively be removably coupled to the guidewire body as described above. An optional polymeric insert may be provided as part of a coupling to reduce electrical emission during operation of the device.

The plaque removal assembly may be fixedly or movably disposed at the distal end of the hollow guidewire body. If the plaque removal assembly is movable, the plaque removal assembly may be movable from a first axially retracted position (or extending distal to the hollow guidewire body) to a second position which is longitudinally distal to the first position. The drive shaft of the present invention may be axially movable and rotatable within the axial lumen of the hollow guidewire body. In an embodiment, either or both the guidewire and the drive shaft may be coated with any one or more or combinations of hydrophilic coatings and therapeutic agents. In an embodiment, the guidewire is coated with heparin or other similar therapeutic agents. In an embodiment, the drive shaft may be coated with Teflon® or other materials to improve the rotation of the drive shaft within the guidewire axial lumen.

In use, the access system can be delivered to the target site over a conventional guidewire. Once the access system has been positioned near the target site, the conventional guidewire can be removed and the elongate member (e.g., hollow guidewire) of the present invention can be advanced through an inner lumen of the access system to the target site. Optionally, the support system can be delivered concurrently with the advancement of the hollow guidewire. Alternatively, because the elongate member can have the shapeability, flexibility, pushability, and torqueability to be advanced through the tortuous regions of the vasculature, the elongate member may be advanced through the vasculature to the target site without the use of the separate guidewire. In such embodiments, the access system can be advanced over the elongate member of the present invention to the target site. Once the elongate member has been positioned at the target site, the drive shaft is rotated, preferably, in an oscillation rotational mode, and advanced into the occlusive material or the entire elongate member may be advanced distally into the occlusion. The rotation of the drive shaft distal tip creates a path forward of the elongate member. In some embodiments, the path created by the distal tip has a path radius which is larger than the radius of the distal end of the elongate member. In other embodiments, the path created by the distal tip has a path radius which is the same size or smaller than the radius of the elongate member.

The hollow guidewire device can be used in conjunction with conventional guidewires to cross a total occlusion. For example, the hollow guidewire can be used to cross calcified regions (e.g. proximal and distal cap) of the total occlusion requiring more penetration force. A conventional guidewire can be used to cross softer, more tortuous regions of the occlusion that require more flexibility. The hollow guidewire and conventional guidewire can be placed parallel as they are advanced or can be exchanged through one access system. If one guidewire enters sub-intimal space, it may be left in place while another hollow guidewire or conventional guidewire continues advancement in parallel.

The preferred operating mode of rotational oscillation of the drive shaft and the distal tip is of particular benefit to the present invention as it prevents tissue from wrapping around the distal tip of the plaque removal drive shaft. This in turn allows for enhanced penetration through, in and/or out of the occlusive or stenotic material. In an embodiment, the drive shaft is configured for rotational oscillation movement such that the shaft distal tip may be rotated through an angle equal to or less than 360°. The shaft distal tip is then adapted to rotate back in the same manner and amount. In an embodiment, the during each oscillation cycle, the motor is configured to provide from about 100 to about 200,000 revolutions per minute ("rpm"); from about 5,000 to about 50,000 rpm; normally about 12,000 rpm. Typically, the drive shaft is oscillated so that it changes polarity after a period of time. The period of time may range from about 0.2 to about 5.0 seconds, usually in a range from about 0.3 to about 1.2 seconds, and normally about 0.7 seconds. By way of example, in an embodiment, the motor is configured to provide about 140 complete cycles (i.e., rotations of 360°) per about every 0.7 seconds before it oscillates to change the polarity of the rotation.

Advancing may further comprise reciprocating axial translation of the distal tip of the drive shaft so as to completely cross the total occlusion. Oscillation and reciprocation of the drive shaft may be carried out sequentially or simultaneously. Generally, oscillation and/or reciprocation movement of the drive shaft are carried out by a drive motor. However, a device operator may also easily affect reciprocation by simply axially translating the device by its handle manually. Advancing may further comprise extending the drive shaft from a retracted configuration to an extended configuration relative to the distal portion of the hollow guidewire body, wherein the drive shaft is simultaneously or sequentially extended and oscillated.

Proper positioning at the occlusion site may further be verified by viewing a distal end of the hollow guidewire under fluoroscopy via any of the radiopaque components of the devices, such as the coil, gold plating, or the core element distal tip.

Electronic circuitry within the control system of the handle may measure a variety of characteristics for feedback control. For instance, the load encountered during advancement of the distal tip in the body lumen may be measured. For example, a load sensor may be coupled to the motor and configured to provide an output representative of the load on the motor. In an embodiment, an audible and/or visual output may be coupled to the load sensor to provide load status to the user. The audio feedback may be represented in a continuous spectrum or it may be represented as a plurality of discrete load levels. The visual feedback may be represented as a plurality of discrete load levels. In another embodiment, absence of load may be indicative of a break or fracture in the oscillating drive shaft distal tip. A locking mechanism on a distal end of the guidewire body may be provided to further prevent inadvertent release of the distal tip of the drive shaft into the body lumen by locking it to a distal end of the hollow guidewire. Still further, the device may be automatically disabled in response to the no load measurement as an added safety feature. In still another instance, a use of the device based on time or number of revolutions or oscillations may be measured. The device may be automatically and permanently disabled once the measured time or number is above a threshold value. This safety feature protects against device fatigue and warrants that the device is not operable past its optimal lifetime use.

In an embodiment, the present invention provides a kit. The kit has any of the hollow guidewires and/or the drive shafts described herein and instructions for use according to any of the methods described herein. The instructions for use in passing occlusions or stenosis in a body lumen comprise rotational oscillation and advancing either or both the hollow guidewire and the drive shaft into the occlusive or stenotic material to create a path through the occlusive or stenotic material. A package is adapted to contain either or both the hollow guidewire, the core element, and the instructions for use. In some embodiments, the instructions can be printed directly on the package, while in other embodiments the instructions can be separate from the package.

These and other features of the invention will be further evident from the attached drawings and description of the invention.

BRIEF DESCRIPTION OF THE DRAWINGS

FIG. 4 is an elevational view of an exemplary guidewire embodying features of the present invention having an elongate body such as a ribbon/spring longitudinally disposed within the lumen of the guidewire body lumen at its distal region.

FIGS. 4A and 4B illustrate the ribbon of FIG. 4 under unstrained and strained configurations.

FIG. 5B is an elevational view of an exemplary guidewire embodying features of the present invention having a second tube forming the proximal portion of the guidewire body.

FIG. 5C is an elevational view of an exemplary guidewire embodying features of the present invention having a second tube forming the proximal portion of the guidewire body.

FIG. 5D is an elevational view of an exemplary guidewire embodying features of the present invention having a first tube forming the intermediate and the proximal portions of the guidewire body.

FIG. 5E is an elevational view of an exemplary guidewire embodying features of the present invention having a first tube forming the intermediate and the proximal portions of the guidewire body with a spring element in a trained configuration.

FIGS. 6A and 6B, are elevational views of an exemplary guidewire embodying features of the present invention having a slidable member for shaping the distal region of the guidewire body, with FIG. 6B showing the slidable member in an unstrained configuration.

FIG. 9 is an elevation view of an exemplary guidewire embodying features of the present invention with the intermediate tube extending to the distal end of the guidewire body and having a distal end providing spring features.

FIG. 10 is an elevation view of an exemplary guidewire embodying features of the present invention with the intermediate tube extending all the way to the proximal end of the guidewire body and having a polymeric jacket disposed on at least a portion thereof.

DETAILED DESCRIPTION OF THE INVENTION

The systems, devices and methods according to the present invention will generally be adapted for the intraluminal treatment of a target site within a body lumen of a patient, usually in a coronary artery or peripheral blood vessel which is occluded or stenosed with atherosclerotic, stenotic, thrombotic, or other occlusive material. The systems, devices and methods, however, are also suitable for treating stenoses of the body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed at passing through atheromatous or thrombotic occlusive material in a coronary and peripheral arteries, it will be appreciated that the systems and methods of the present invention can be used to remove and/or pass through a variety of occlusive, stenotic, or hyperplastic material in a variety of body lumens. It should be appreciated, that many of the features of the different embodiments as described, may be used in the described embodiment, alone, or together with others.

Figure 1:
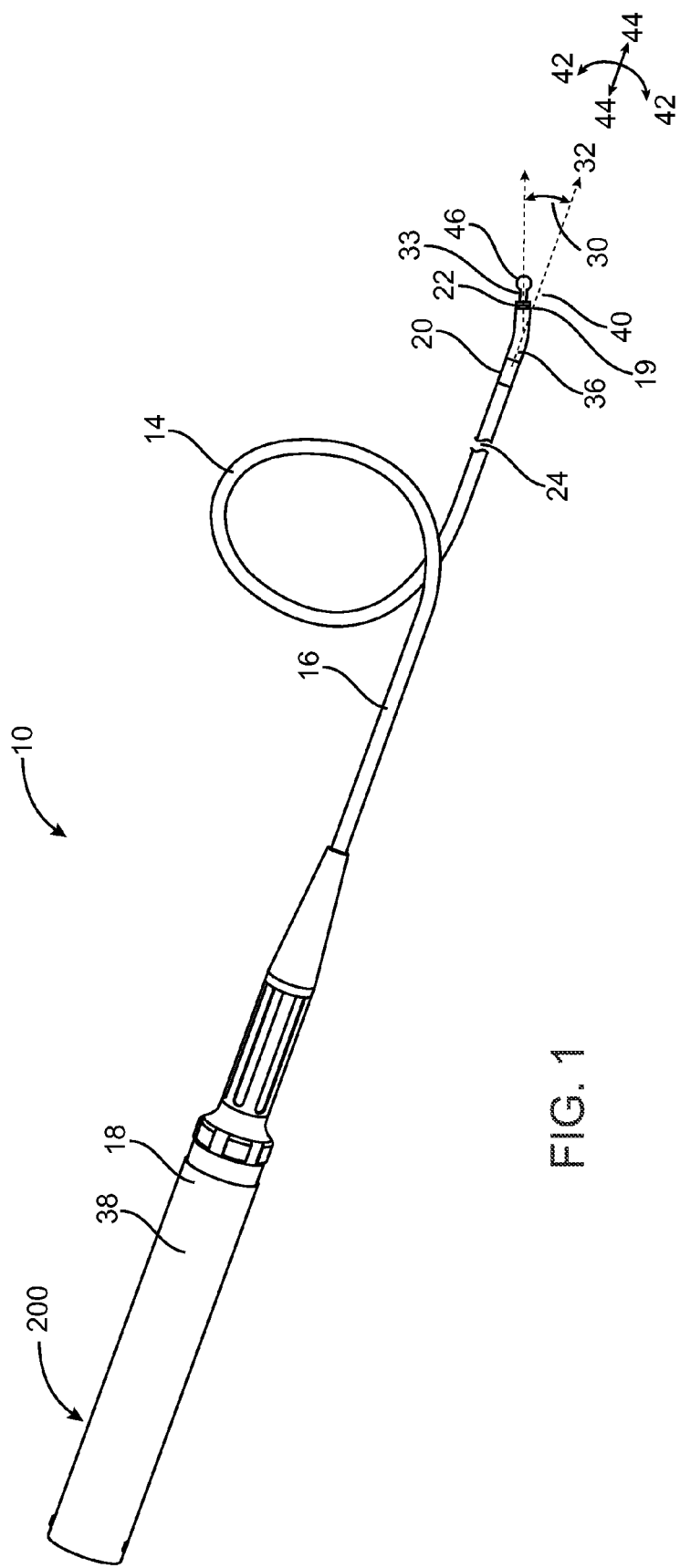
FIG. 1 is an elevational view of a system embodying features of the present invention having a guidewire with shapeable distal region.

An apparatus 10 embodying features of the present invention is illustrated in FIG. 1 generally including an elongate member 14, such as a guidewire; having an elongate body 15 with a proximal portion 16, a proximal end 18, a distal portion 20, a distal end 22, and an axial lumen 24 (or interchangeably used herein "central passage") extending therethrough. A handle assembly 200 may be fixedly or removably attachable to the elongate member 14. In an embodiment as shown, the handle is fixedly attached to the elongate member.

The distal portion 20 of the body 15, includes a shapeable (e.g., malleable) distal region 19. The shapeable region is configured such that it can take a desired shape. By way of example, the distal region 19 is shaped by a physician to have an angle of deflection 30, as compared to a longitudinal axis 32 of the elongate member 14 (i.e., a deflection angle as defined by the tangential line formed between the distal end 22 of the body 15 and the longitudinal axis 32). In an embodiment, the distal region 19, is at least substantially, preferably, parallel to the longitudinal axis 32 (e.g., the deflection angle is zero "0"). The shapeable distal region 19 is configured to be shaped depending on the choice of the physician in one or more number of ways such as manually, setting of the desired angle via a tool, or any other suitable means. In an exemplary embodiment, the distal region 19 is configured to be manually shaped. The distal region 19, after it has been shaped, may take on a deflection 30, generally, ranging from about 0 to about 90 degrees ("°"), usually from about 0 to about 60°, and normally from about 5 to about 45°. In an embodiment, the deflection, after having been shaped, is about 15°, about 30°, or about 45°. The length of the shaped region may range from about 0.1 cm to about 4.0 cm, from about 0.2 cm to about 2.0 cm, from 0.2 cm to about 1.0 cm. The deflection 30 of the distal region 19 may be arrived at in a smooth transition or in an abrupt transition, or any type and degree of transition in-between. One or more shapes may be placed into the distal region 19 of the body 15. In an embodiment, the 0.5 cm distal length of the body as measured from the distal tip 46 of the core element 33 and may be shaped to 30° angle, with a 15° angle shape extending proximally 0.5 cm from the 30° region.

The apparatus 10 may further comprise a plaque removal assembly, such as a core element 33 comprising a drive shaft 36 and a distal tip 46, for removing tissue and creating a path through the body lumen. The drive shaft 36 has a shaft proximal end 38 and a distal end 40 and is received within the axial lumen 24 of the hollow guidewire 14. In an embodiment, the core element is configured for any one or more of rotation, oscillation, translation, and axial movement within the lumen 24, as for example shown by arrows 42 and 44.

In an embodiment, the core element may be configured for rotation (with or without oscillation) but not axial movement. The distal tip 46 of the core element 33 at the shaft distal end 40 may have a shaped profile, enabling the movement or positioning of the distal tip 46 beyond the distal end 22 of the body 15. The rotation of the core element 33 may be used to create a cutting path forward of the distal end 22 of the hollow guidewire body for passing through the occlusive or stenotic material in the body lumen. The drive shaft 36 and the distal tip 46, may independently be formed from stainless steel or nitinol, or other suitable material including other radiopaque materials such as platinum/tungsten compounds. The proximal end 18 of the body 15 may be coupled to a vacuum source or a fluid source (not shown) such that the target site can be aspirated or infused during the procedure, if desired.

Figure 2:
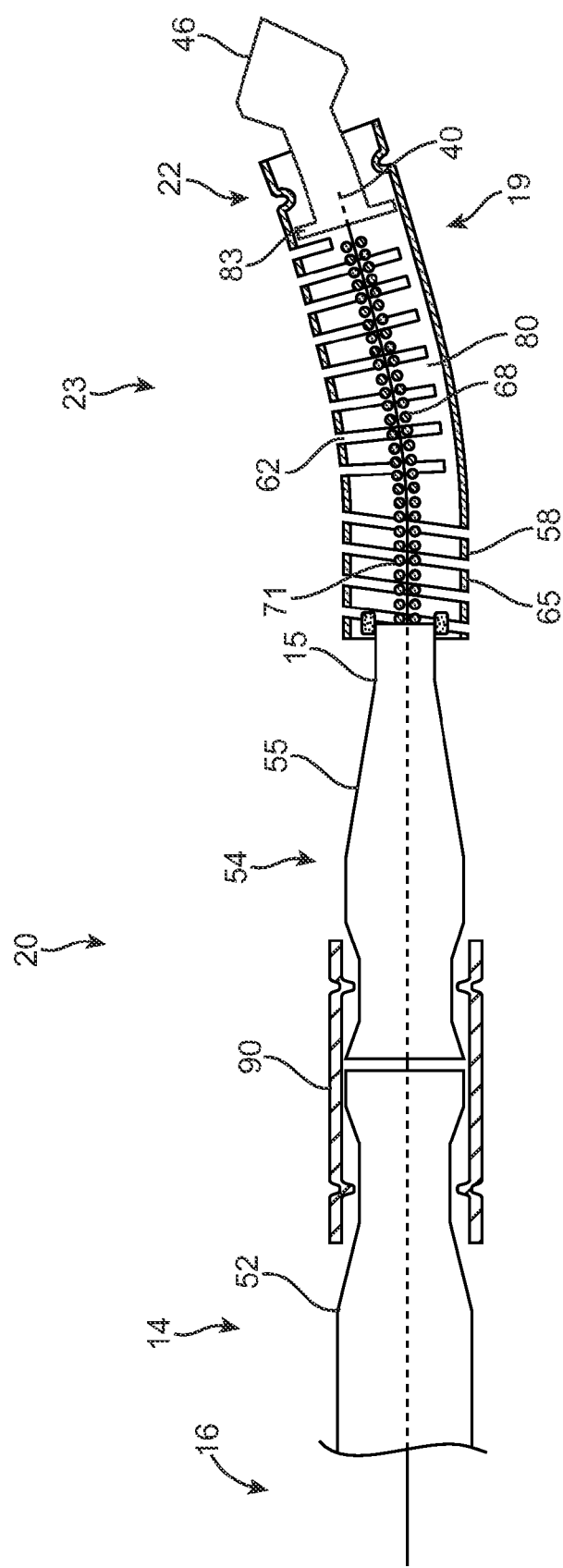
FIG. 2 is an elevational view of a distal end of an exemplary guidewire embodying features of the present invention having multiple portions.

Now referring to FIG. 2, wherein like references represent like elements, an exemplary embodiment of a distal portion 20 including the shapeable distal region 19 such as that shown in FIG. 1 is shown. It should be noted that in all figures, unless otherwise stated, the shapeable distal region 19 is shown after it has been shaped by the user to have the desired deflection angle.

The body 15 includes the proximal portion 16, an intermediate portion 54, and distal portion 20 The intermediate and proximal portions as shown, are formed from first and second solid wall tubes, 55 and 52, respectively. The distal portion 20 of the body 15 includes a distal section 23 which includes the shapeable distal region 19 and optionally a non-shapeable region 58 (or less shapeable as compared to the shapeable distal region 19). It should be noted that the body 15 may be formed from one or more tubular members. By way of example, the body 15 may be formed from a single tubular member with different configurations such as solid outer shell or a shell with slots formed therein a least along a portion thereof.

In some exemplary embodiments, the first tube 55 is distally tapered. In an exemplary embodiment, the tapered first tube has a longitudinal dimension ranging from about 20 to about 60 cm, usually about 30 or about 40 cm. In an exemplary embodiment, the first tube, has an outer diameter ranging from about 0.005 to about 0.040 in., from about 0.008 to about 0.018 in., normally about 0.011 in.

In the embodiment shown, the first tube, at its proximal end is engaged with the distal end of the second solid wall tube 52, and at its distal end with the proximal end of the distal portion 20 not shown in FIG. 2. As shown, a cuff 90, surrounds the two ends of the first tube and the second tube by press fitting, soldering, or other suitable means. The cuff may be formed from suitable material such as stainless steel, nickel-titanium, or platinum-iridium. Additionally, the elongate intermediate segment may be at least partially covered with a coil or polymer (such as PEBAX).

The distal section 23 of the distal portion 20 may be formed of either or both slots (ribs) 62 and helical pattern including interrupted helix 65. Optionally, and as shown, an coil 68 is disposed around, and extends proximally from, the distal end 40 of the drive shaft. The coil 68 radially separates the drive shaft from the distal section 23 of body 15. The coil 68 is, preferably, formed from stainless steel or a radiopaque material such as platinum-iridium. The coil 68 may be soldered, glued, or otherwise attached to the inner surface of the guide wire body. In an embodiment, the coil 68 may float without being fixedly attached between the shaft and the body 15. The coil (liner) 68 may have any desired length and pitch. In the embodiment shown, the coil 68 has a longitudinal dimension substantially the same as that of the distal section 23 of the body 15. However it should be noted that that the coil may extend further proximally as may be necessary. The coil generally has a longitudinal dimension from about 1 and 200 cm, from about 1 to about 10, normally about 4 cm.

As shown, the shapeable distal region 19 and the less-shapeable distal region 58 of the distal section 23 are formed from a single tubular member with varying physical characteristics (e.g., flexibility, slots, helix). In some embodiments, the proximal portion 16, the intermediate portion 54, and the distal portion of the body 15 may be independently, formed from stainless steel, nitinol, polymeric material, radiopaque material including platinum such as platinum/iridium compounds, or a combination thereof.

In an embodiment, the distal portion 20 may have a longitudinal dimension ranging from about 1 to about 200 cm, from about 10 to about 80 cm, from about 20 to about 40 cm, normally about 35 or about 30 cm. In an embodiment, the shapeable distal region 19 extends from about 0.1 to about 10 cm, usually from about 0.2 to about 1, normally about 0.5 cm. In an embodiment, all or at least a portion of the distal section 23 of distal portion 20 may be plated with suitable radiopaque material, such as gold. The shapeable distal region 19 may include slots (ribs) 62 or helix (or interrupted helix) 71 or any suitable configuration as described earlier above. In the embodiment shown, the distal section 23 in its entirety includes slots and helix.

In some exemplary embodiments, the body 15 may be formed from a unitary construction formed from a single hypotube. It should be noted, that various features may be used in one or more embodiments without departing from the scope of the invention.

As shown, at least a section of the distal portion 20 forming the distal section 23, may be laser edged to create a plurality of helical windings or spirals 65 (as described earlier above). The laser cuts may extend all the way from the proximal end to the distal end of the body, or a portion thereof, preferably at least along the length of the distal section 23. The laser cuts used to create the helical windings 65 may extend completely through a wall 80 of the distal section 23 or may extend only partially through the wall so as to create thinner wall portions (e.g., grooves).

The laser edging removes at least a portion of the material from the guidewire body 15. The laser cuts, may be, in the form of an interrupted helical pattern ranging from about 90° to about 270°, preferably about 180°. Interruptions or breaks, when present have no laser cuts and are in a range from about 5° to about 225°, preferably 30° segments. In embodiments, including the interruptions help preserve the integrity and continuity of the device 14, particularly when it is steered through tortuous blood vessels. The interrupted helical pattern may have a clockwise or counterclockwise helical direction and a kerf ranging from about 0.0005 inches ("in.") to about 0.0040 in. The helical windings may have the same or variable pitch through at least part of the distal section 23. As can be appreciated, the pitch between adjacent windings will affect the flexibility of the hollow guidewire 14. As can be appreciated, the hollow guidewire 14 may comprise any number of sections, and the sections in turn may have any desired pitch or kerf, any number or degree of helical windings or interruptions, clockwise or counterclockwise helical directions, any length, or variations thereof.

As described above, the distal section 23 of the guidewire may comprise the same or different patterned sections such as radial slots, openings, and/or thinned portions. In an exemplary embodiment, the slots may extend along the length of the distal section 23 of the hollow guidewire. The radial slots/openings may be formed on the guidewire body 14 by way of laser cutting or electro-discharge machining (EDM) that removes at least a portion of the material from the guidewire body, as described above with respect to the helical windings. The slots/openings may extend around less than the entire circumference of the hypotube, typically extending between about 25% (e.g., 90°) to about 90% (e.g., 324°) of the guidewire body. Support ribs typically will extend between 100% (e.g., 360°) to about 25% (e.g., 90°) around the circumference of the hollow guidewire body 14.

The pitch between helical windings 65 may decrease in the distal direction so as to provide the hollow guidewire 14 with increasing flexibility in the distal direction. In an exemplary embodiment, it may be desirable to have sections of the guidewire body to have no helical cuts or have laser cuts that have a pitch that increases in the distal direction so as to provide less flexibility over a portion of the hollow guidewire.

Figure 3:
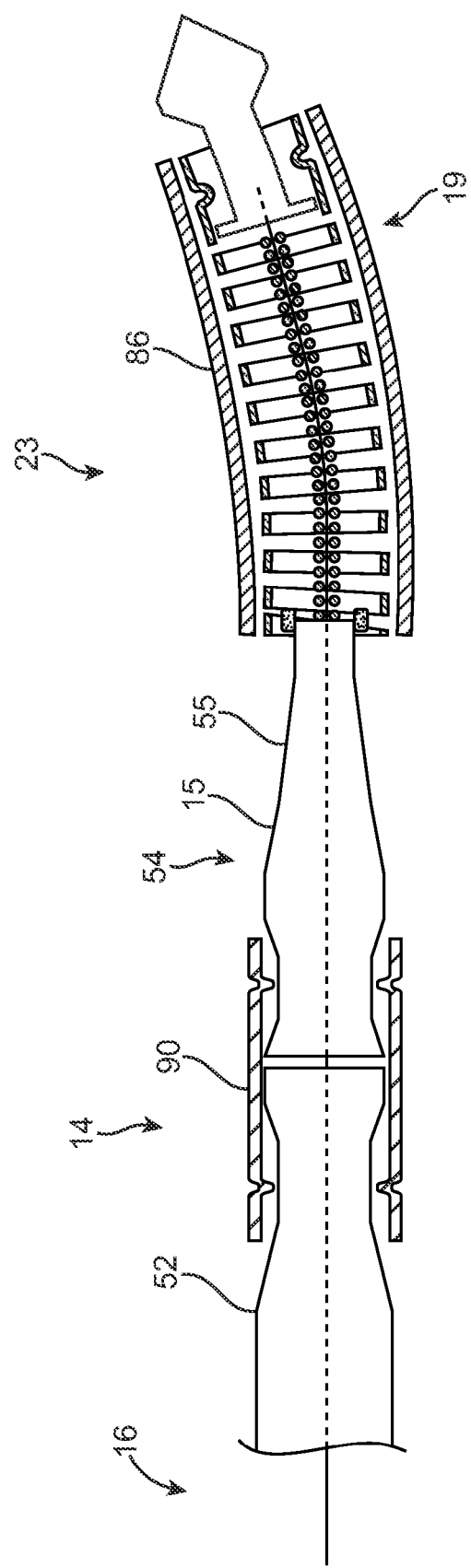
FIG. 3 is an elevational view of a distal end of an exemplary guidewire embodying features of the present invention having a polymeric jacket disposed around the distal section of the guidewire body.

In an embodiment features of which are shown in FIG. 3, the distal section 23 of body 15 includes a polymeric jacket 86 on at least a portion of the outer surface of the distal section 23. The polymeric jacket may be used to bring about the desired shape of the shapeable distal region 19. By way of example, the polymeric jacket is formed from a steam sensitive polymer. To achieve the desired shape, in operation, one may apply steam to the polymer at the distal section 23 including the shapeable distal region 19. In an embodiment, the polymeric jacket may be disposed over or under the distal section 23, or it be used alone as the distal section 23 of the body 15.

In an embodiment, features of which are shown in FIG. 4, wherein like references represent the like elements, the shapeable distal end is, at least in part, arrived at by way of a spring or an elongate body such as a metal wire or ribbon 50, longitudinally disposed in the shapeable distal region 19, preferably within the hollow guidewire inner lumen 24, between coil 68 and the body 15. The spring 50 is formed from shape memory material to assume an arcuate memory (e.g., nickel-titanium alloy, heat set to the assume an arcuate memory) when it is not under strain (as shown in FIG. 4A). By way of example, when the shapeable distal region 19 of the body 15 is straightened through plastic deformation, the preshaped ribbon/spring, now under strain (FIG. 4B), conforms to the straightened configuration of the guidewire. Thereby, when the shapeable distal region 19 of the body 15 is shaped by the user into a desired curve through plastic deformation, the pre-shaped ribbon provides shape retention during use, until straightened again by the user.

The elongate body/spring 50 (such as metal wire or ribbon) may be formed from suitable shape memory material such as stainless steel, nitinol, nickel-titanium, or cobalt-chromium; and has a longitudinal dimension ranging from about 0.1 to about 6 centimeters ("cm"), from about 0.2 to about 1 cm. In an embodiment, the spring/metal wire or ribbon 50 has a longitudinal dimension of about 0.3 cm. The ribbon or spring may be attached; at its distal, proximal, or both ends; (e.g., fixedly or otherwise, such as soldered) to the guidewire body.

Figure 5A:
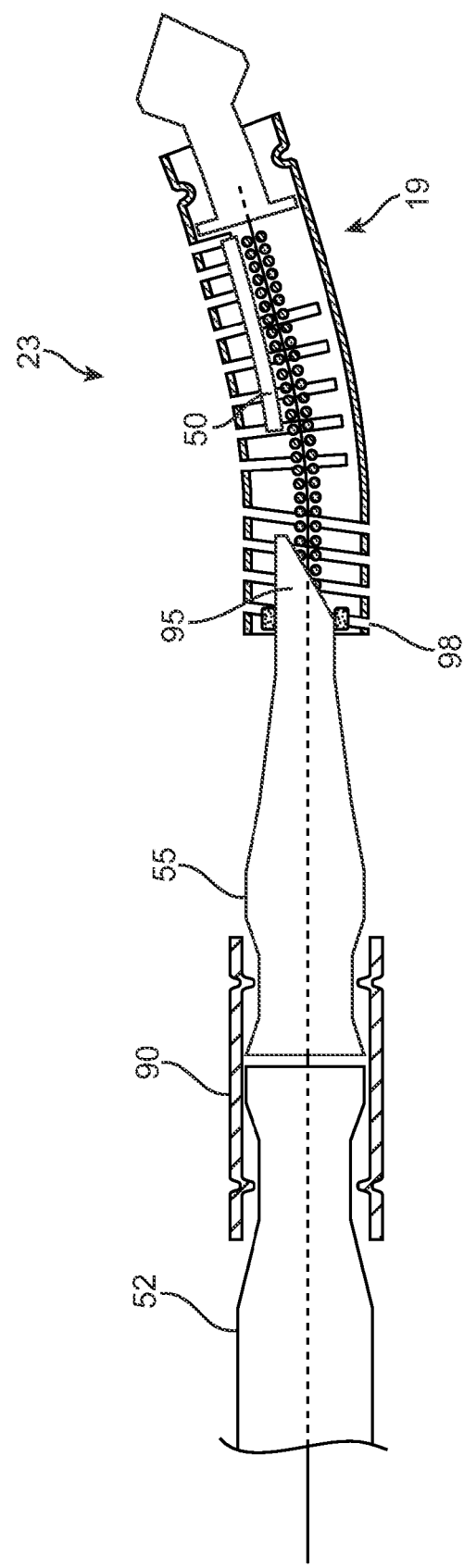
FIG. 5A is an elevational view of an exemplary guidewire embodying features of the present invention having an intermediate portion with a distal end extended within the proximal portion of the helical distal section of the guidewire.

Now referring to FIG. 5A, in an exemplary embodiment, wherein like references refer to like elements, the first tube 55 is further distally tapered having a first tapered distal end 95 and extends distally beyond a proximal end 98 of the distal section 23, preferably, as shown, terminating proximal to the shapeable distal region 19.

In an embodiment features of which are shown in FIG. 5B, wherein like references represent like elements, a portion of the body 15 is shown, having a second tube 52 formed from stainless steel hypotube which forms the proximal portion 16, and a first tube 55 (such as a nitinol) which forms the intermediate portion 54. The first and second tubes are joined via cuff 90. The guidewire is shown in an unshaped configuration. The spring 50 in a strained configuration is shown attached to the body 15 (e.g., via solder) along at least a portion of the shapeable distal region 19. The distal end 40 of the drive shaft 36 is secured (e.g., laser welded) to the core element distal tip 46. The first tube 55 such as a nitinol hypotube, is further distally tapered for increased flexibility with a first tapered distal end 96 further tapered and extending within the distal section 23. The coil 68 (e.g., formed from stainless steel), as previously shown, extends along the distal section 23 radially separating drive shaft 36 from the distal section 23. The distal section 23 with the helix/slots (interrupted helix) is laser cut from stainless steel tube. The drive shaft 36 is formed from nitinol wire and is tapered under the shapeable distal region for increased fatigue life. In the embodiment shown, the distal section 23 has a longitudinal dimension of about 4 cm, a 40 cm flexible length which extends from the distal tip of the core element to the distal end of the cuff, with an overall working length of 165 cm extending from the distal tip of the core element to its proximal end.

Now referring to FIG. 5C, a portion of the body 15 is shown with a shapeable distal region being in the shaped configuration and the spring 50 in the unstrained configuration. The superelastic nitinol shaping spring 50 in this configuration minimizes plastic deformation of the laser cut stainless steel distal section, which otherwise may cause an unwanted shape change.

Now referring to FIG. 5D, a portion of the body 15 is shown with a first tube 105 (e.g., formed from nitinol hypotube 101) further replacing the second tube 52, and extending the full proximal length of the guidewire without the second tube (e.g., stainless steel hypotube) or cuff 90. The spring 50 as shown is in the strained configuration with a stainless steel distal section 23.

Now referring to FIG. 5E, the guidewire of FIG. 5D, is shown with spring 50 in an unstrained configuration.

Now referring to FIGS. 6A and 6B, an exemplary embodiment of a hollow guidewire is shown wherein like references refer to like elements. A slidable member 110, extends along an exterior of a distal portion of the first tube 55, and extends distally through the inner lumen of the distal section of the hollow guidewire body 15. The slidable member terminates at the distal end 22 of the body 15. The slidable member 110, may take on any suitable shape such as a ribbon or wire/spring. The slidable member 110 at its proximal end is engaged with the first tubular member 55 at a proximal stop 117, by way of suitable means such as friction or multiple locking features. The slidable member 110, acts similarly to spring 50 shown and discussed earlier. As illustrated in FIG. 6B, the slidable member is shown in unstrained configuration with a shaped distal section.

The slidable member is processed to have a memory shaped configuration prior to use. The axial movement of the sliding member proximally causes the angle at the distal end of the hollow guidewire member to decrease while the distal axial movement of the slidable member increases the angle.

Figure 7:
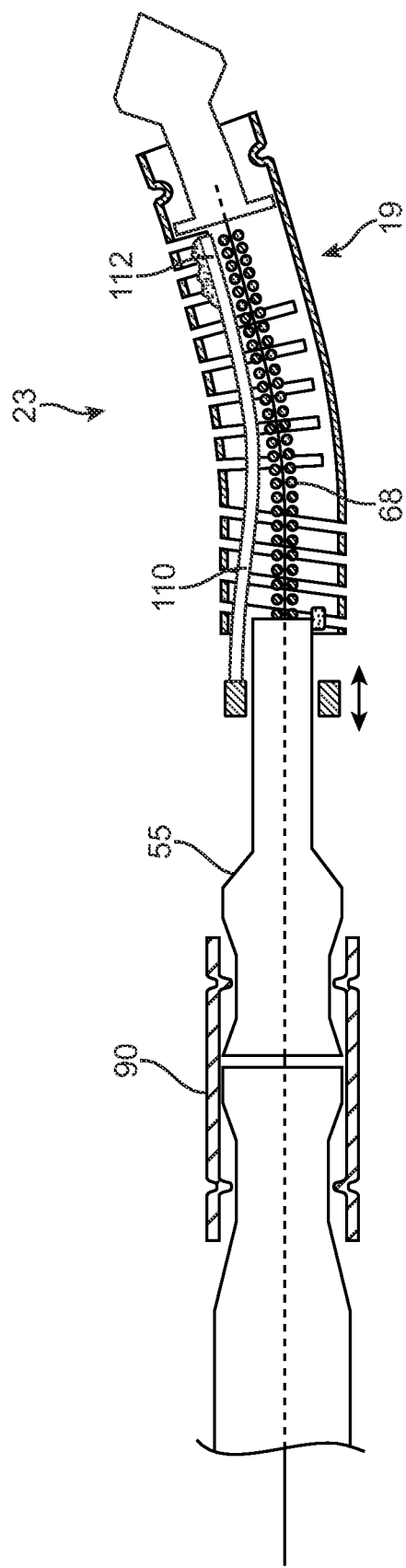
FIG. 7 is an elevational view of an exemplary guidewire embodying features of the present invention having a slidable member secured to the distal of the guidewire body for shaping the distal region of the guidewire body.

Now referring to FIG. 7 distal end 112 of the slidable member 110 is secured to the distal end 22 of the body 15, by suitable means such as soldering, as shown. It may be secured in place between the coil and the distal end 22 of the guidewire. The slidable member may be formed from suitable material such as nitinol or stainless steel.

Figure 8:
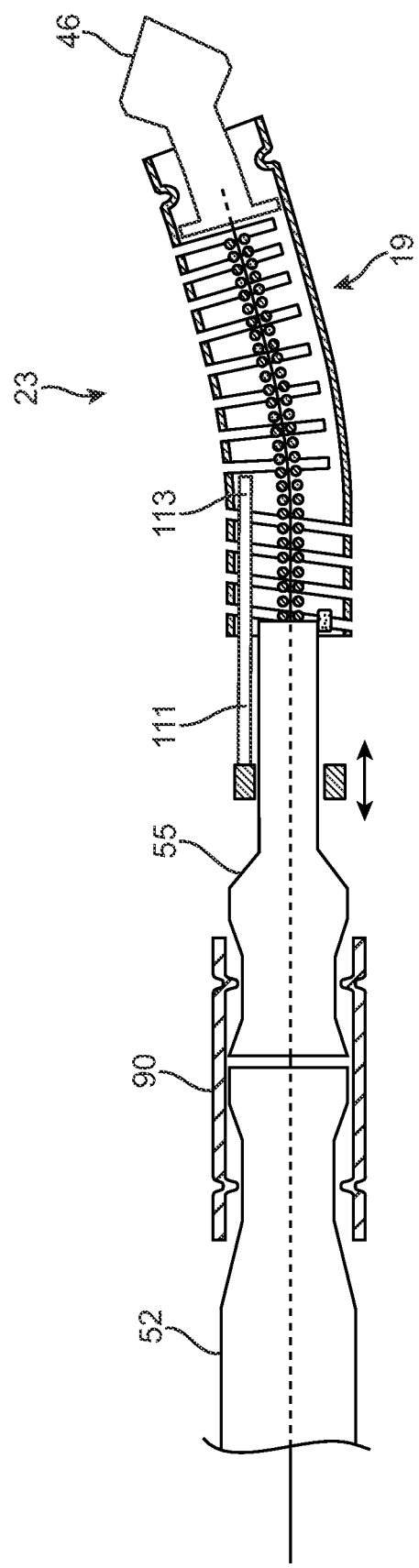
FIG. 8 is an elevation view of an exemplary guidewire embodying features of the present invention with the shapeable distal region 19 formed from a shape memory alloy having an arcuate memory shape.

Now referring to FIG. 8, in an exemplary embodiment, the distal section 23 is formed from a shape memory material with the shapeable distal region 19 having an arcuate memory shape (e.g., heat set nitinol). Member 111 is a slidable elongate member which does not function as the same as spring 110 descried previously and is processed to have a straight configuration with a distal end 113. When the sliding member 111 is advanced distally, the ribbon/wire straightens the shapeable distal region thus allowing the user/physician to shape the distal region 19 to the desire angle. When the sliding member is pulled proximally and the ribbon is removed from under the shapeable distal region of the guidewire, the shapeable distal region returns to its memorized pre-shaped configuration.

Now referring to FIG. 9, in an embodiment, the first distally tapered end 95 (e.g., skived) of the first tube 55 may be further tapered forming a second tapered portion 97. The second tapered portion 97, is shaped similarly to the elongate member/spring 50, and extends distally to the distal end 22 of the body 15. The tapered (skived) distal portion 97 may be preshaped and perform similarly to that discussed in reference to FIG. 4.

As described above, the drive shaft 36 is disposed within the axial lumen 24 of the guidewire body 14 with the core element tip 46 extending distally from the distal end 22 of the body 15. The distal tip 46 may be formed from stainless steel or nickel-titanium and a tip end (not shown) formed from a radiopaque material, such as a platinum-tungsten compound. The radiopaque material of the tip may be disposed within the tip body by suitable means such as solder or swaging.

Now referring to FIG. 10, the first tube 105 extends proximally and may be engaged with the second 52 (not shown) at a farther proximal point than previously shown. In some embodiments the second solid wall tube 52 (e.g., stainless steel hypotube) may not be present at all, with the first tube 105 forming also the proximal portion of the body 15, similar to that discussed in reference to FIG. 5F, such that it continues proximally to the handle assembly (e.g. 200) without the need for the second tube 52 forming the proximal portion (e.g., formed from stainless steel) or any other means of coupling or cuff.

Additionally and optionally, at least a portion of the first tube may be partially covered with a polymer jacket 130 (e.g., PTFE, polyester, etc.) over the nitinol intermediate portion to increase lubricity, diameter, and/or friction.

Figure 11:
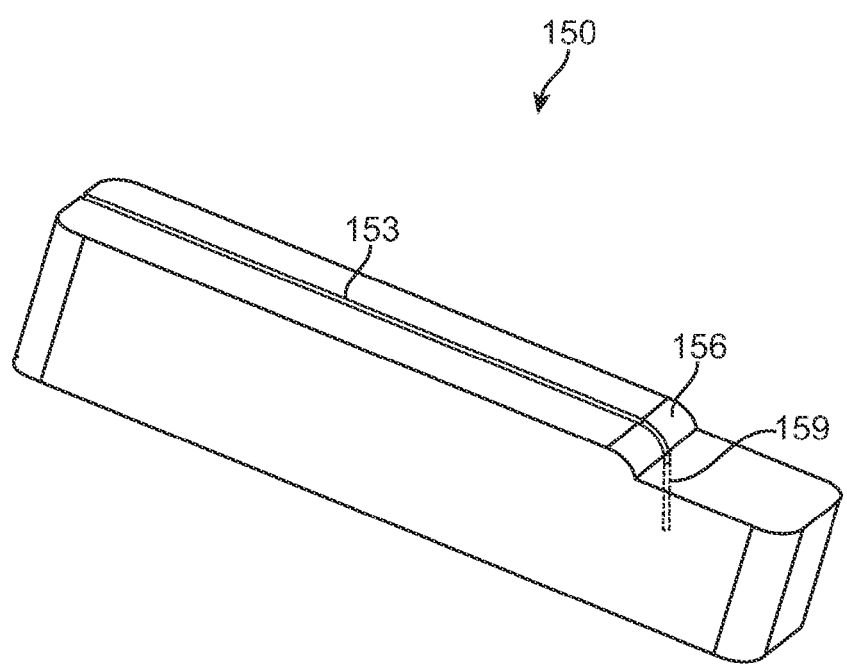
FIG. 11 is an elevation view of an exemplary shaping tool 150 for shaping and controlling the angle and the length of the shapeable distal region of the hollow guidewire body.

Now referring to FIG. 11, an exemplary shaping tool 150 for shaping and controlling the angle and the length of the shapeable distal region 19, is shown. Such shaping tool may be provided alone or in combination with the shapeable guidewire in a kit. As shown, the shaping tool includes a groove 153 for housing the guidewire body 15, a curved surface 156 and a bore 159 for affecting the length and the angle of the shapeable distal region. In use, the guidewire body 15 is placed inside/along the groove by the user/physician, and running along the curved space and inserted into the bore 159 until the distal end 22 of body 15 reaches the bottom of the bore. The guide wire is thereafter bent over the curved surface 156. The bore depth and the curved surface, affect the length of the shapeable distal region, while the bore angle and curve surface determine the angle of the shapeable distal region. The shapeable distal region length and angle may also be affected by the shaping spring 50 (which is part of the guidewire), dimensions, length, location, and the memorized shape.

Figure 12:
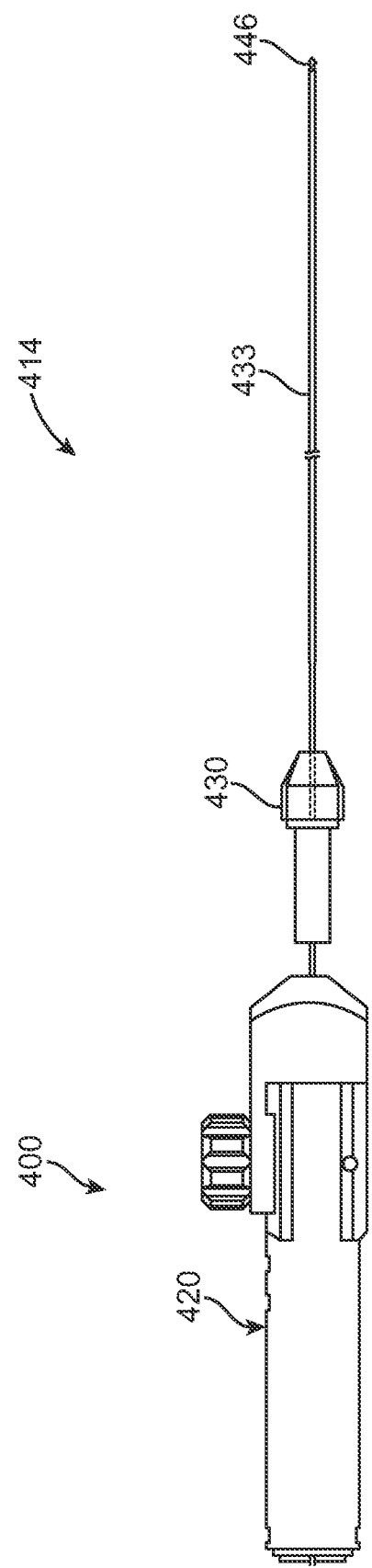
FIG. 12 is an elevation view of an exemplary system 400 including a shapeable hollow guidewire similar to that of FIG. 1 in straight configuration.

Now referring to FIG. 12, wherein like references refer to like elements, a system 400 including a shapeable hollow guidewire 414 similar to that of FIG. 1 is shown in straight configuration. The shapeable guidewire includes a core element 433 terminating at a distal tip 446. The hollow guidewire and the core element proximally terminate in housing 420. An adjustable torquer 430 is placed between the housing and a portion of the guidewire which extends distally therefrom.

Figure 13:
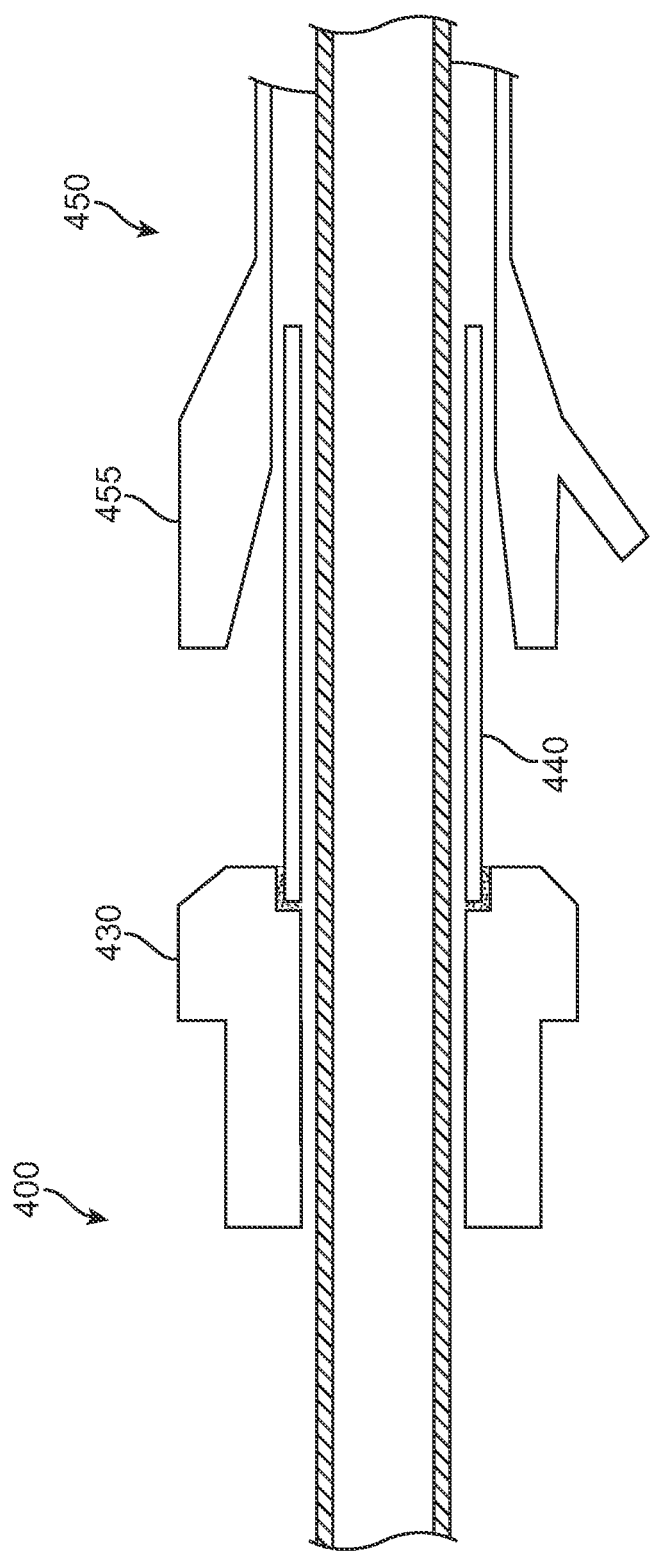
FIG. 13 is an elevation view of an exemplary embodiment of a system including a support catheter.

Now referring to FIG. 13, a portion of the system 400 extends proximally and distally from the adjustable torquer 430 which is placed over the exterior of the hollow guidewire 414. Distal to the adjustable torquer 430 a support catheter 450 is shown having a flange 455 for introducing the hollow guidewire if its use is necessary or chosen by the physician/user into the support catheter. An optional stainless steel tube 440 is attached to the adjustable torquer 430 and extends distal to the proximal end of the support catheter 450.

Figure 14:
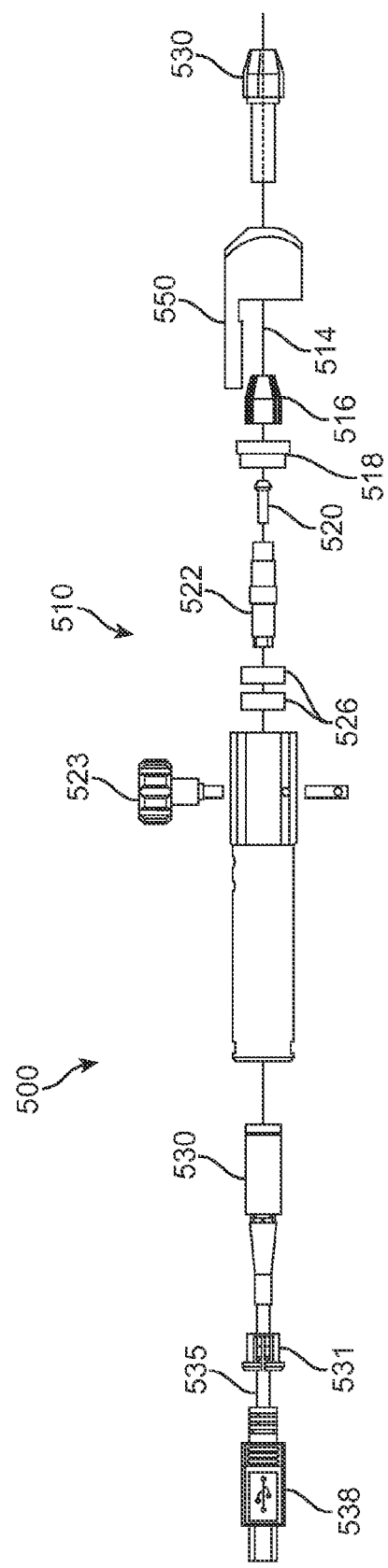
FIG. 14 is an elevation view of another embodiment of a system embodying features of the present invention.

Now referring to FIG. 14, a proximal portion 510 of a system 500 is shown embodying features of an exemplary system. The proximal portion of system 500 at its proximal end includes the adjustable torquer 530, a cover 550 placed over a portion of the hollow guidewire 514, and a spindle nose 516 which connects to the spindle. A collet 520, partially contained within the spindle, which secures the hollow guidewire by tightening the spindle nose 516. The spindle 522 is inserted through the bearings 526 into the cylinder. The spindle cap secures the spindle 522 into the cylinder. The detachable feature 523 allows for the optional detachment of the hollow guidewire from the housing, enabling the hollow guidewire to be extended for use with over the wire catheter exchangers. As shown, the core element extends proximally into the housing and connects to a motor 530 via a motor coupling. The motor is contained within the cylinder. A cable 535 is connected to the motor 530 and to a USB connector 538 for controlling its various modes of movement.

Figure 15:
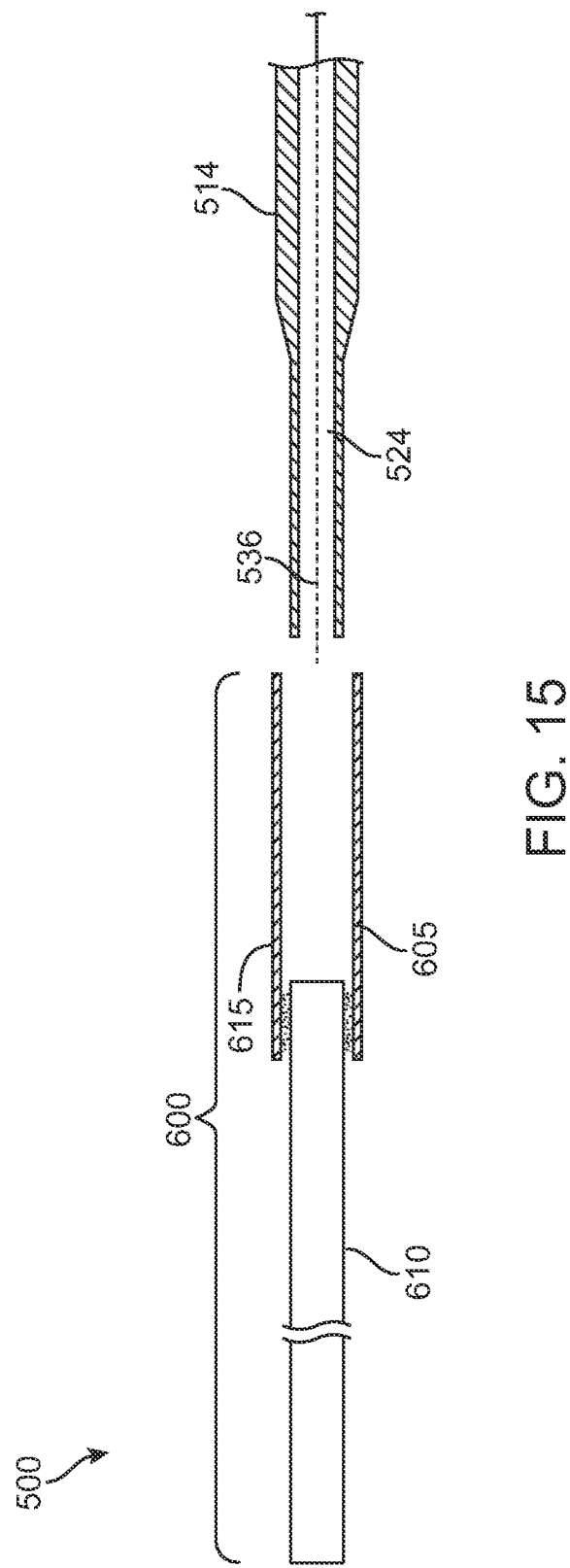
FIG. 15 is an elevation view of the system of FIG. 14 after the guidewire has been detached from a housing.

Now referring to FIG. 15, a portion of the system 500, after the guidewire has been detached from the housing is shown. Hollow guidewire 514 with a lumen 524 extending through, houses the core element 533. An extension wire 600 at its distal end is connected to the hollow guidewire 514. The extension wire 600 includes a stainless steel or nitinol hypotube 605 and is connected to a stainless steel or nitinol wire 610, with a proximal end of the hypotube 605 forming a lap joint 615 with the distal end of the wire 610.

While not explicitly illustrated, a person of ordinary skill in the art will recognize that aspects of one configuration of the hollow guidewire body may be used with other configurations of the hollow guidewire body. Therefore, the above description should not be taken as limiting the scope of the invention which is defined by the appended claims.

What is claimed is:

1. A shapeable guidewire for crossing an occlusion or stenosis within a body lumen, said guidewire comprising:
    a guidewire body having a proximal end, a distal end, and a central passage therethrough, wherein a distal region of the body is malleable so that said distal region may be manually configured to a desired curved shape; and
    a mechanically driven core element disposed in the central passage and passing out through the distal end of the guidewire body, wherein the core element may be rotated, within the central passage while the distal region of the body retains its desired curved shape;
    wherein the core element includes a cutting element that creates a cutting path when rotated.

2. A guidewire as in claim 1, wherein the malleable distal region comprises a tube formed from a malleable metal.

3. A guidewire as in claim 2, wherein the tube has a length and is slotted at least along a portion of said length.

4. A guidewire as in claim 3, wherein one or more slots are formed along a helical spine of the tube.

5. A guidewire as in claim 4, wherein the one or more slots along the helical spine have interruptions.

6. A guidewire as in claim 3, wherein one or more slots are formed along an axial spine of the tube.

7. A guidewire as in claim 2, wherein the tube has a length and is cut into a helical ribbon along at least a portion of said length.

8. A guidewire as in claim 1, further comprising a spring element disposed along at least a portion of the malleable distal region wherein the spring element is aligned to help hold the desired curved shape.

9. A guidewire as in claim 8, wherein, the spring element disposed along the at least portion of the malleable distal region comprises a strained linear spring element axially aligned along one side of the at least a portion of the malleable distal region, wherein the spring element has an arcuate memory and is configured to help hold an arc manually formed in the at least a portion of the malleable distal region when not under strain.

10. A guidewire a in claim 8, wherein the spring element is formed from a shape memory material.

11. A guidewire as in claim 8, wherein the malleable distal region and the core element are at least partially separated by a liner.

12. A guidewire as in claim 11, wherein the liner is at least in part a coil.

13. A guidewire according to claim 1, wherein the malleable distal region comprises a heat-sensitive component that is configured to be softened by heating.

14. A guidewire as in claim 13, wherein the heat-sensitive component comprises a polymer jacket disposed along at least a portion of the malleable distal region.

15. A guidewire according to claim 1, wherein the guidewire body is formed from either or both a first and a second solid walled tube.

16. A guidewire according to claim 15, wherein the first solid walled tube extends proximally from at least a longitudinal portion of the malleable region to the proximal end of the guidewire.

17. A guidewire according to claim 15, wherein the first solid walled tube extends proximally from at least a longitudinal portion of the malleable region, and a distal end of the second solid walled tube which extends to the proximal end of the guidewire body.

18. A guidewire according to claim 15, wherein the first solid walled tube and the second solid walled tube are formed, respectively, from nickel titanium and stainless steel.

19. A guidewire according to claim 1, wherein a housing is disposed at the proximal end of the guidewire body and contains a motor for moving the core element.

20. A guidewire according to claim 19, wherein the motor is attached to a controller system.

21. A guidewire as in claim 20, wherein the controller causes the motor to rotate the core element.

22. A guidewire according to claim 21, wherein the controller oscillates the core element at a preset rotational speed and changes rotational direction at a preset period.

23. A guidewire as in claim 1, wherein the core element comprises a drive shaft formed from nickel titanium.

24. A guidewire according to claim 1, wherein the proximal end of the guidewire body is configured for attachment to a distal end of an extension body.

25. A method for crossing a luminal occlusion, said method comprising:
    providing a shapeable guidewire;
    manually shaping a distal end of the guidewire to impart a desired curved shape;
    advancing the guidewire through an occlusion while a core carried by the guidewire is mechanically rotated to engage and penetrate the occlusion while the distal end of the guidewire;
    wherein the core includes a cutting element that creates a cutting path when rotated.

26. A method as in claim 25, wherein the core is rotated as the guidewire is advanced.

27. A method as in claim 25, wherein manually shaping comprises shaping a spring element at the distal end of the guidewire, wherein the spring element helps to hold the curved shape of the distal end of the guidewire as the core is rotated.

28. A method as in claim 27, wherein the distal end of the guidewire comprises a slotted tube.

29. A method as in claim 25, further comprising advancing the guidewire while the core is not being rotated.

* * * * *